United States Patent
Slater et al.

(10) Patent No.: US 11,783,262 B2
(45) Date of Patent: Oct. 10, 2023

(54) AUTOMATIC DETECTION AND GENERATION OF MEDICAL IMAGING DATA ANALYTICS

(71) Applicant: Canon Medical Systems Corporation, Otawara (JP)

(72) Inventors: Benjamin Roy Slater, Elk River, MN (US); James E. Rosenthal, St. Paul, MN (US); Joseph John Fromm, Minneapolis, MN (US)

(73) Assignee: Canon Medical Systems Corporation, Otawara (JP)

(*) Notice: Subject to any disclaimer, the term of this patent is extended or adjusted under 35 U.S.C. 154(b) by 304 days.

(21) Appl. No.: 16/762,412

(22) PCT Filed: Nov. 20, 2018

(86) PCT No.: PCT/US2018/062060
§ 371 (c)(1),
(2) Date: May 7, 2020

(87) PCT Pub. No.: WO2019/104061
PCT Pub. Date: May 31, 2019

(65) Prior Publication Data
US 2020/0356935 A1    Nov. 12, 2020

Related U.S. Application Data

(60) Provisional application No. 62/589,929, filed on Nov. 22, 2017.

(51) Int. Cl.
*G06Q 10/06*        (2023.01)
*G06Q 10/0637*    (2023.01)
(Continued)

(52) U.S. Cl.
CPC ..... *G06Q 10/06375* (2013.01); *G06F 3/0482* (2013.01); *G06N 5/04* (2013.01);
(Continued)

(58) Field of Classification Search
CPC ........ G06Q 10/06375; G06Q 10/06312; G06F 3/0482; G06N 5/04; G06N 20/00;
(Continued)

(56) References Cited

U.S. PATENT DOCUMENTS 10,748,072 B1*  8/2020  Seeger .................. G06N 7/005
2007/0083389 A1  4/2007  Dyer et al.
(Continued)

FOREIGN PATENT DOCUMENTS

WO    WO-2019104061 A1    5/2019
WO    WO-2019104061 A8    5/2019

OTHER PUBLICATIONS

"International Application Serial No. PCT/US2018/062060, International Search Report dated Feb. 1, 2019", 2 pgs.
(Continued)

*Primary Examiner* — Robert A Sorey
*Assistant Examiner* — Kimberly A. Sass
(74) *Attorney, Agent, or Firm* — Schwegman, Lundberg & Woessner, P.A.

(57) ABSTRACT

An information system and user interface to enable the analysis of clinical data for operational improvement and issue identification in medical imaging procedures is disclosed. In an example, opportunity and usage analytics are generated from relevant imaging procedure data (e.g., radiology procedure data) through operations including: obtaining clinical data that indicates usage of imaging resources to perform medical imaging procedures; analyzing the usage of the imaging resources from the clinical data, to identify values of opportunities for predicted changes to the usage of
(Continued)

the imaging resources; and generating a visualization of the values of the opportunities for output in a graphical user interface, the visualization indicating values of opportunities relative to past usage and predicted changes to the usage of the imaging resources. Further examples also enable a detailed visualization and interaction with data for a particular opportunity in relation to medical facilities, organizations, modalities, and staffing resources.

22 Claims, 6 Drawing Sheets

(51) Int. Cl.
| | | |
|---|---|---|
| *G16H 70/60* | (2018.01) | |
| *G16H 40/20* | (2018.01) | |
| *G16H 15/00* | (2018.01) | |
| *G16H 30/20* | (2018.01) | |
| *G16H 50/70* | (2018.01) | |
| *G16H 50/20* | (2018.01) | |
| *G16H 70/20* | (2018.01) | |
| *G06N 20/00* | (2019.01) | |
| *G06F 3/0482* | (2013.01) | |
| *G06N 5/04* | (2023.01) | |
| *G06Q 10/0631* | (2023.01) | |
| *A61B 5/00* | (2006.01) | |
| *A61B 5/055* | (2006.01) | |
| *A61B 6/03* | (2006.01) | |
| *A61B 8/00* | (2006.01) | |

(52) U.S. Cl.
CPC ....... *G06N 20/00* (2019.01); *G06Q 10/06312* (2013.01); *G16H 15/00* (2018.01); *G16H 30/20* (2018.01); *G16H 40/20* (2018.01); *G16H 50/20* (2018.01); *G16H 50/70* (2018.01); *G16H 70/20* (2018.01); *G16H 70/60* (2018.01); *A61B 5/0035* (2013.01); *A61B 5/055* (2013.01); *A61B 6/032* (2013.01); *A61B 8/00* (2013.01)

(58) Field of Classification Search
CPC ........ G16H 15/00; G16H 30/20; G16H 40/20; G16H 50/20; G16H 50/70; G16H 70/20; G16H 70/60; A61B 5/0035; A61B 5/055; A61B 6/032; A61B 8/00; A61B 6/5217; A61B 6/566; A61B 8/5223; A61B 8/565
See application file for complete search history.

(56) References Cited

U.S. PATENT DOCUMENTS

| | | | |
|---|---|---|---|
| 2012/0010901 A1* | 1/2012 | Johnson | ................ G16H 40/60 705/2 |
| 2012/0066677 A1* | 3/2012 | Tang | ..................... G06F 9/4856 718/1 |
| 2013/0066646 A1 | 3/2013 | Backhaus et al. | |
| 2014/0079297 A1* | 3/2014 | Tadayon | .............. G06V 40/172 382/118 |
| 2014/0164008 A1 | 6/2014 | Gordon et al. | |
| 2015/0082228 A1* | 3/2015 | Cantor | ................. G06T 11/206 715/771 |
| 2015/0213222 A1 | 7/2015 | Amarasingham et al. | |
| 2016/0092641 A1 | 3/2016 | Delaney et al. | |
| 2016/0378917 A1 | 12/2016 | Sharafshahi et al. | |

OTHER PUBLICATIONS

"International Application Serial No. PCT/US2018/062060, Written Opinion dated Feb. 1, 2019", 10 pgs.

* cited by examiner

AUTOMATIC DETECTION AND GENERATION OF MEDICAL IMAGING DATA ANALYTICS

PRIORITY CLAIM

This application is a U.S. National Stage Filing under 35 U.S.C. 371 from International Application No. PCT/US2018/062060, filed on Nov. 20, 2018, and published as WO 2019/104061 on May 31, 2019, which application claims the benefit of priority to U.S. Provisional Patent Application Ser. No. 62/589,929, filed Nov. 22, 2017, which are incorporated herein by reference in their entireties.

TECHNICAL FIELD

Embodiments pertain to data processing techniques and configurations used with information networks and informatics systems. Further embodiments relate to the evaluation, identification, and processing of information available in medical diagnostic and evaluative settings such as in medical imaging environments.

BACKGROUND

As healthcare processes have become increasingly digitized, large volumes of clinical data are now generated on human patients at nearly every medical facility for many types of healthcare interactions. However, as the volume of data has increased, the complexity of retrieving, interpreting, and drawing useful conclusions from the data points in such clinical data has also increased. This challenge is caused, in part, from the variability of the amount and type of clinical context available from data for a given patient, and the multiple ways that data collecting processes vary within medical practices.

As one example, medical imaging data is captured in many aspects of diagnostic and evaluative workflows, from a variety of different medical providers and in many different settings. Given the volume of medical imaging data that is captured by respective medical practices, administrators of such medical practices often struggle to make evidenced-based management decisions about how to efficiently utilize and operate medical workflows and allocate technological and human resources. This is complicated by the fact that imaging operations are complex, extremely valuable, and extremely expensive. Because advanced data analytics and statistical analysis are beyond the skills of most people and many medical practices, optimizations are not applied or discovered for imaging operations and many other medical settings.

DETAILED DESCRIPTION

Figure 1:
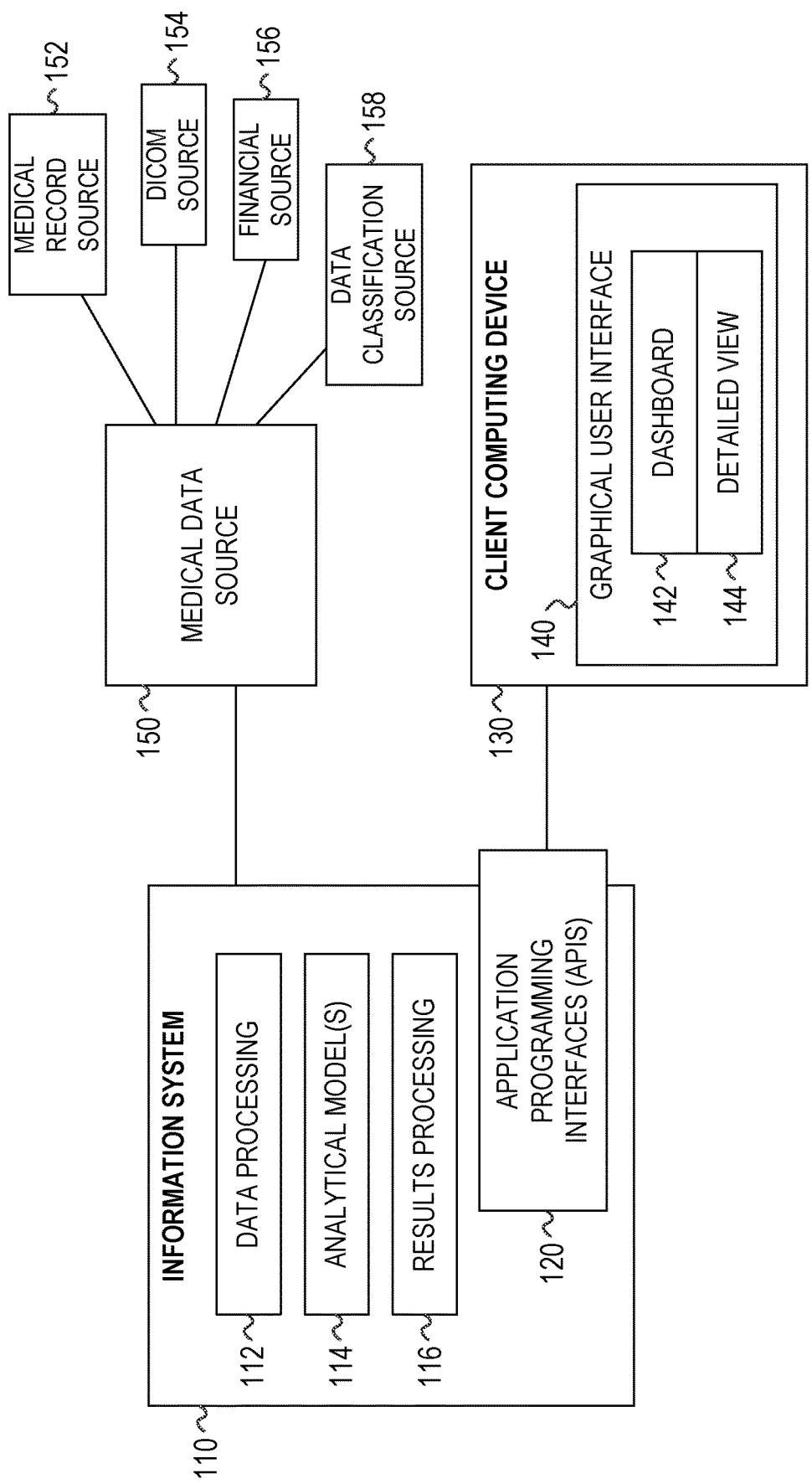
FIG. 1 illustrates an overview of a system for performing medical imaging data analytics according to an example described herein.

The following description and the drawings sufficiently illustrate specific embodiments to enable those skilled in the art to practice them. Other embodiments may incorporate structural, logical, electronic, process, and other changes. Portions and features of some embodiments may be included in, or substituted for, those of other embodiments.

The present disclosure illustrates various techniques and configurations operable with an information system to enable the automatic collection, analysis, and output of analytics and other forms of information retrieval. As discussed herein, this analytics and information retrieval may be provided for clinical and medical-related data from disparate data sources. The various techniques and configurations specifically provide techniques of generating actionable analytics for a variety of medical imaging scenarios that are not available in conventional approaches. However, it will be understood that other forms of medical data (and data from other technological fields) may also be utilized with the following approaches.

In an example, algorithms may be defined and deployed to incorporate imaging domain expertise and offer advanced analytics to be presented in various forms of data visualizations and dashboards. These algorithms may be deployed in data processing scenarios to combine business, operational, and clinical data to automatically detect anomalies and quantify the value of data characteristics in specific and human-understandable terms. Such algorithms may be used, for example, to prioritize opportunities using confidence scoring and impact scoring algorithms to derive relevance for a user. The graphical output and visualizations produced from such algorithms also may be used to quantify the value or results associated with any identified anomalies, patterns, or outcomes.

Medical imaging practices often struggle to make evidence-based management decisions. This occurs, in part, because advanced data analytics and statistical analysis is beyond the skills of most people, and because existing data analytics solutions require significant overhead to identify and describe search problems. Further, such search problems, sources of issues, and possible opportunities for improvements are often undefined and unknown. The techniques described herein combine business, operational, and clinical data from disparate sources to identify issues and prescribe actions that may be used to improve operational outcomes.

In an example, an information system (and accompanying sub-systems and interfaces of this information system) is designed to automatically quantify information relevant to operational activities. This information may be used to extract and identify issues that the user may not even know exist, and dynamically prescribe actions that may help the user correct the problem. As discussed herein, this approach may be surfaced by specific algorithms of the information system that are used to analyze data and quantify specific "opportunities" from different "opportunity types." Each "opportunity type" may utilize or be produced from a unique algorithm that leverages advanced statistical analysis and medical imaging domain expertise. Although such respective opportunities may be associated with business-relevant goals or objectives, the references to opportunities and opportunity types are used to refer to dynamically identified and processed data types that are relevant to some technology-based resource or technology-based resource utilization.

In an example, respective opportunities are identified to be visualized on a "smart board" dashboard graphical user interface, which is used to organize and display such opportunities for comparison and selection for more details. The respective opportunities may be ranked or arranged on a chart, graph, or other measurement output according to a "confidence" algorithm and a value of the opportunity measured by some metric (e.g., financial metrics, resource benefit metrics, etc.). This dashboard graphical user interface includes functionality to allow a user to compare the opportunities, identify or filter a particular opportunity or opportunity type, select an opportunity, and obtain prescriptive information that supports the achievement of the opportunity. Further, this interface allows the ranking and scoring of confidence in particular opportunities and opportunity recommendations. The prescriptive recommendations themselves are ranked using an impact scoring algorithm. In this manner, an opportunity can serve in a role of an identifiable "issue", and the opportunity ranking, scoring, or comparison may identify the importance or severity of the issue relative to some benchmark or metric.

As will be apparent, the following operations and system configurations may be used to address a number of technical problems within computer and information processing fields, and related information location, query, classification, and categorization problems within clinical applications of information technology. In the context of the following examples, some of the technical problems addressed include: prioritized and efficient processing of a large volume and large number of sources of clinical data; suitable processing prioritization and data-driven workloads based on conditions; accuracy and efficiency measurements of such technological and clinical workflows and the accompanying computer data operations (e.g., to reduce errors, reduce the amount of data being processed, and reduce the amount of time needed to process); and the accessibility of resources (both computer resources and medical resources) which often leads to shortages and inefficiencies.

As discussed in the following examples, specific reference is made to a number of medical diagnostic, interpretation, and treatment settings, particularly with use of medical imaging processes. However, it will be understood that the technical problems addressed with the present disclosure are not limited to medical or business process improvements; rather, the disclosed processing techniques address the functioning of underlying medical information systems and data processing networks that are essential to modern medical practices. Thus, the application of the present techniques to data analysis in other scientific and academic disciplines and technical fields will be apparent.

Further, the data processing approaches discussed herein provide a number of benefits that extend beyond medical imaging informatics into a variety of technical fields. With the use of the present techniques, computing processing of medical information data sets may be automated and improved significantly. Such computing may result in improved automation of previously manual activities, causing a reduction in errors and inaccurate activities, and improved efficiency of software operations and associated processing and networking hardware resources. Further, the techniques provide improvements over conventional approaches for creating, organizing, and producing analytics for medical information data content, allowing improved computational results and improved graphical outputs in reduced time. The integration of the present techniques with analytical models, rules, defined user inputs, and electronic commands also provides a mechanism in which technological enhancements provide an improvement and tangible benefits over conventional and manual ways of analyzing such data and issues.

FIG. 1 illustrates an overview of a system for performing medical imaging data analytics, an according to an example described herein. As shown, an information system 110 is designed to capture, identify, and process analytical data, as part of a procedure to identify various forms of opportunities and opportunity types, based on data from a medical data source 150. As discussed herein, the information system 110 is designed to drastically simplify the process of presenting users with relevant data required to identify and impact opportunities (including revenue and cost aspects of such opportunities) for medical procedure environments involving medical imaging, and specifically, radiology practices. In particular, the use of the information system 110 is described in the following to produce a predictive and historical application of statistical analysis and data visualizations, incorporating business logic and domain expertise for the optimization of medical imaging procedures (such as radiology scans) and resources (such as modalities, technicians, physicians, and schedules) used with such imaging procedures. Thus, as used herein, references to "resources" may refer to measurable aspects of some entity used in an imaging procedure, with an individual resource potentially referring to a scanner, a set of machines, a technician, a radiologist, a radiology practice at a site, etc.

The information system 110 includes software or logic which implements one or more application programming interfaces (APIs) 120 used to serve or provide the analytical data to a data consumer. In an example, the information system 110 includes data processing functionality 112, analytical model functionality 114, and results processing functionality 116, to exchange data with a client computing device 130 via the APIs 120. Although FIG. 1 depicts a client-server arrangement, with the information system 110 as server and the computing device 130 as a client, it will be understood that the functional components may be embodied in other examples on a single computing device (e.g., via a server-hosted process, such as operable via a web site; or via a client-hosted process, such as a set of client software applications and data sources operating on a single system).

The data processing functionality 112 operates to identify, extract, and transform relevant medical data related to the field of analysis, such as medical imaging procedures. The data processing functionality 112 may pre-process such medical data and load the data into a data warehouse or other data store at the information system 110. The analytical models (in analytical model functionality 114) include executable or operable models, which incorporate algorithms, operations, and processes for accomplishing analysis or related analytical functions for opportunities based on the processed data. The analytical models may, in some examples, include aspects of machine learning or artificial intelligence features, including pre-trained models and networks (e.g., neural networks). The results processing functionality 116 includes features that provide usable outputs for identifying and interacting with opportunities, including organizing listings of opportunities, rankings of opportunities, and the like.

The APIs 120 may be utilized via methods called with a graphical user interface 140, which hosts user-interactive features for interaction and visualization with relevant opportunity data and data functions. An operative user may utilize a user-interactive dashboard 142 and a detailed view 144 of the graphical user interface 140, as user actions are received in the graphical user interface 140. These user actions then request data values via API calls relating to the identified opportunities and opportunity types. Example implementations of the APIs 120, the dashboard 142, and the detailed view 144, are provided in the following sections and figures.

In the space of medical imaging, conventional data analysis techniques are capable of offering only basic descriptive analytics. For instance, to produce some analytical results with prior approaches, a user must define a question, find the data sources required to answer that question, build a query to aggregate the data, conduct analysis, identify a problem, root cause, or answer to the question, and identify what actions might be relevant to the problem. The information system 110 is designed to utilize advanced predictive and prescriptive analytic techniques to automatically or dynamically perform each of these operations, while presenting analytical data in the graphical user interface 140 that a user can directly consume to take action.

The medical data source 150 may include a plurality of sources from a plurality of vendors. Thus, while conventional techniques may provide analytics views only from data in a single vendor-specific database, the medical data sources 150 may be provided from a combination of one or more medical record (e.g., HL7) data sources 152, imaging (e.g., DICOM) data sources 154, financial (e.g., billing systems) data sources 156, and data classification (e.g., CMS, and ICD-10) data sources 158. Further, the information system 110 (accessed via a mechanism such as via the APIs 120) may transform or convert the medical data into another format, to provide analytics and usable information that is agnostic of the data source.

In an example applicable to medical imaging workflows, various JSON APIs may be implemented among server and client operations of the information system 110 and client device 130 to obtain and exchange information relating to medical facilities, sites, and modalities, involved with the medical imaging workflows. In addition to algorithms provided in the analytical models, other algorithms may be deployed among the server and client operations of the system 110 and client device 130. For instance, specialized computations and data values may be invoked in connection with identifying, valuing, or evaluating opportunities in medical imaging procedure improvement scenarios.

In an example, the opportunities that are identified among a plurality of resources may include the following categories of opportunities: 1) Resource utilization; 2) Scheduled vs. Actual usage deviation; 3) Referral change (e.g., decrease in referrals from another medical provider); and 4) Idle time optimization. In the context of radiology procedures, idle time and resource utilization may be analyzed to help identify opportunities for increased usage; scheduled vs. actual usage may be analyzed to help identify opportunities for improved usage or scheduling; referral change may be analyzed to help identify opportunities for changes in workflow and scheduling. Other opportunity variations related to usage, scheduling, and deviation will be apparent from the following categories.

Resource Utilization Opportunities. In a first example, an analytical model implements an algorithm to compute and identify resource utilization revenue and savings opportunities logic (e.g., from use of an individual resource such as a scanner, facility, radiology practice, etc.). The computations performed for resource utilization may include: (a) Linear computations performed to identity one or more relationships between: exam volume and utilization, revenue and exam volume, and cost and exam volume; and (b) Standard deviation calculated with an inbuilt expression in PostgreSQL Upper Sigma (upper control limit) may be calculated by adding standard deviation to average utilization. Lower Sigma (lower control limit) may be calculated by subtracting standard deviation from average utilization.

The identified opportunities for resource utilization may include: (1) Resource Utilization Revenue Opportunities—When average utilization for a particular facility, modality, and resource is between Upper Sigma and Lower Sigma; (2) Resource Utilization Saving Opportunities—When average utilization for a particular facility, modality, and resource is less than Lower Sigma.

Resource utilization opportunity may be assessed for the following dimensions: (1) Health System; (2) Facility; (3) Modality; (4) Resource. A Confidence Score for a capacity optimization opportunity for each resource may be pre-computed and filtered. For changes in the filter, the average of the confidence score of the matching records is the resultant confidence score. The opportunity computation may be performed for a pre-defined set of analysis period based on the filter options provided to the user. In an example, this is computed for 30, 60, 90, 180, 365 and 730 days.

Scheduled vs Actual Usage Opportunities. In a second example, an analytical model implements an algorithm to compute and identify schedule opportunities from analyzed medical data. This medical data is captured at a facility and modality level. (Facility and modality level data may also be used to compute opportunities for other dimensions). This algorithm may include the following operation flow:

(1) For each imaging modality (scanner), find the procedure mix performed on that modality for each day in the selected period.
(2) Exclude procedures for which there is no scheduled time data in the Procedures table.
(3) For each remaining procedure, find the time deviation from the scheduled time.
(4) Remove outliers based on set threshold (e.g., exclude exams with a duration of <=3 minutes or more than 180 minutes—via a configurable threshold).
(5) Find the total time deviation from all the remaining procedures.

In further examples, operations may be performed to find the average procedure time duration for the exams conducted on this scanner for that day (average procedure time can be computed using the actual procedure time for all the procedures conducted by that technologist on that day). Operations may be performed to calculate the number of additional procedures that could possibly be done on this scanner on that day, if the total time deviation from step 5 is greater than this procedure time duration. If the count of additional procedures is greater than zero, it would represent a revenue opportunity.

To quantify the revenue from the additional exams, revenue may be projected based on the revenue from the existing procedure mix conducted on that scanner. The steps 1 to step 8 may be repeated for all the scanners across all the facilities.

In a further example, scheduled vs. actual usage of a resource (e.g., an imaging modality) may be further adapted or evaluated based on one or more of the following dimensions:

(1) Health System;
(2) Facility;
(3) Modality;
(4) Resource;

(5) Technologist;
(6) Patient Type.

This analysis may include the generation of a Confidence Score for Scheduled vs. Actual time deviation opportunity, which is derived from the composition of the procedures on which the opportunity was identified.

Referral Drop Opportunities. In a third example, an analytical model implements an algorithm to compute and identify referral drop opportunities, based on a decrease in referrals for medical imaging procedures (e.g., referrals to conduct some scan, as referred from another physician or medical provider). This algorithm may include the following operation flow:
(1) For each referring provider, identify the total outpatient referrals received in the analysis period for a given modality type;
(2) Based on this count, identify average expected outpatient referrals in the last month (or the last quarter) for that modality type;
(3) Compare the expected referral count with the actual referrals in the last month (or the last quarter);
(4) If the expected referral count is greater than actual referrals, it can be presented as a revenue opportunity;
(5) The difference is counted as the additional exams that could have been done, which is used to compute projected revenue from these additional exams based on the revenue from the actual exams conducted.

In a further example, Referral Drop opportunity may be assessed for following dimensions:
(1) Health System;
(2) Facility;
(3) Modality;
(4) Specialty.

Data may be grouped by either Facility or Modality table to form the aggregated data at a Health system level. For changes in the Facility and Modality filter, the average of the confidence score of the matching records is the resultant confidence score.

Idle Time Optimization Opportunities. In a fourth example, an analytical model implements an algorithm to compute and identify resource optimization opportunity, such as with modality non-usage (inactive time, or, idle time). The algorithm may include the following operation flow for identifying optimization opportunities:
(1) For each resource, find the total idle time between exams for the analysis period. Consider idle time during the course of the planned time. The planned time for a resource may be based on its modality type and the facility it belongs to.
(2) Find the average total idle time and standard deviation, grouping resources at a modality level.
(3) Compare total idle time of each resource with the average total idle time of the corresponding modality type.
(4) If the total idle time for compared resource is greater than the average +1 standard deviation, then the resource is identified as one with an improvement opportunity.
(5) Perform step 1 to 4 for all resources.

In a further example, resource optimization opportunities may be assessed for following dimensions:
(1) Health System;
(2) Facility;
(3) Modality;
(4) Resources.

Because a resource is ideally tagged to a facility and modality type, opportunity data may be identified for a resource grouped by facility and modality, and this data may be used for displaying opportunities in other required dimensions.

APIs for Accessing and Generating Opportunity Analytics. In various examples, respective APIs may be designed to provide a variety of values in connection with opportunity analysis in the information system (e.g., communicated from information system 110, to client computing device 130 and GUI 140, via APIs 120). The following list of APIs is not exhaustive, but rather is representative of the type of functionality which may be incorporated into the information system 110 and its data processing functionality 112, analytical model functionality 114, and results processing functionality 116. Further, the following functions may be implemented independently of APIs.

Figure 2:
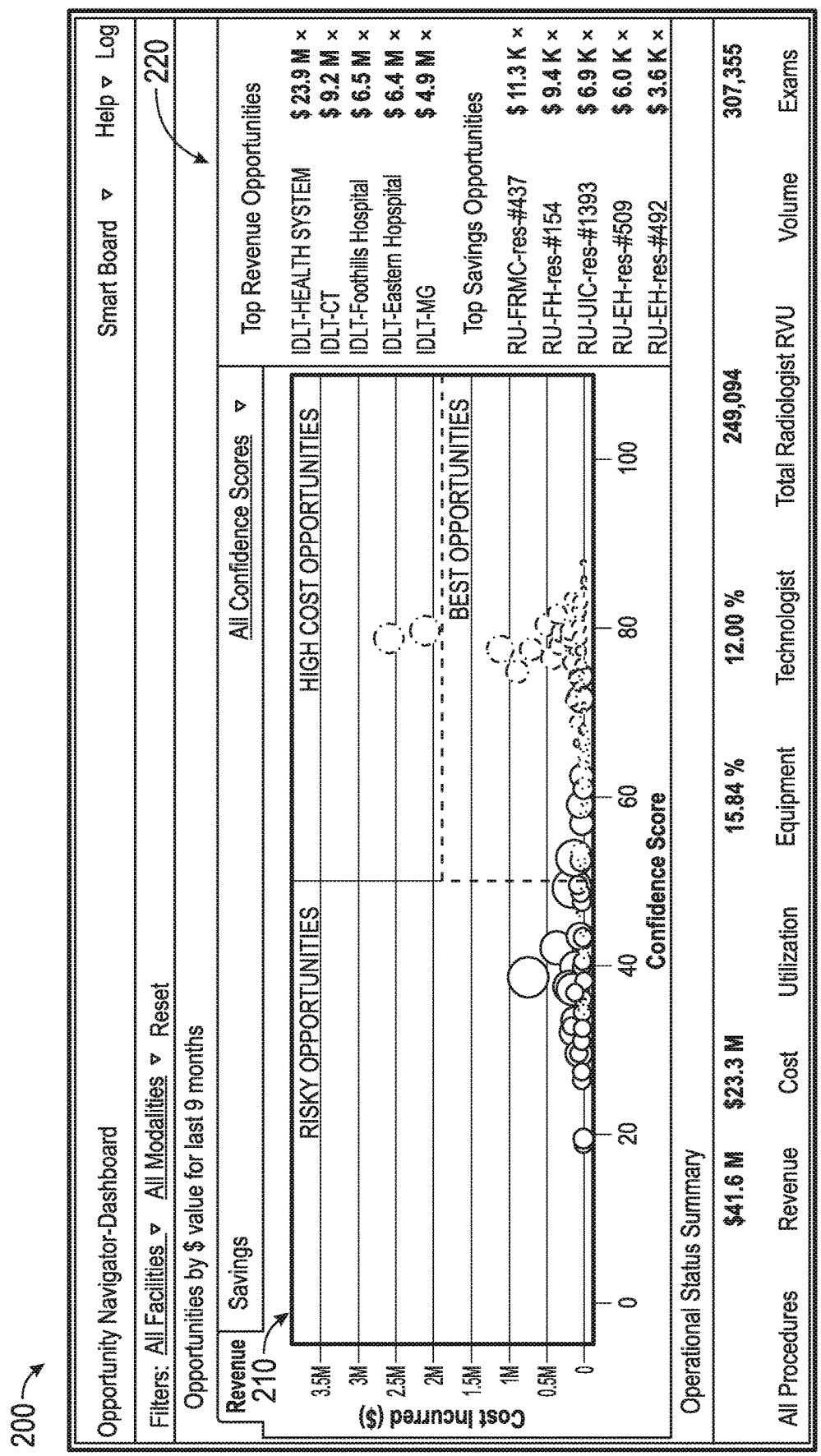
FIG. 2 illustrates a first graphical user interface of a data analytics system according to an example described herein.

In an example, the set of APIs includes an API that enables retrieving all the revenue and saving opportunities based on the selected filters (e.g., filters selected in the dashboard GUI 200 depicted in FIG. 2, discussed further below).

In an example, the set of APIs includes an API that enables displaying the procedures conducted on a Modality for the analysis period, and that returns procedures and their corresponding exam volume, revenue per exam and the time taken to conduct a procedure.

In an example, the set of APIs includes an API that enables displaying the referral count of exams that were referred for the Modality and Facility, and that returns a referral count for a period of time (e.g., the last 90 days or 30 days) as well as revenue loss due to fall in referrals.

In an example, the set of APIs includes an API that enables displaying metrics on an organizational statistics ribbon (e.g., a GUI ribbon), where the organizational statistics ribbon displays value for profit margins, utilization, revenue, cost, exam volume and referral volume in a dashboard user interface (e.g., within the dashboard GUI 200).

In an example, the set of APIs includes an API that enables displaying relevant data on organizational statistics by selected opportunity, where the organizational statistics ribbon displays value for profit margins, current exam day, revenue, and cost in a dashboard user interface (e.g., within the dashboard GUI 200).

In an example, the set of APIs includes an API that enables displaying the statistics on the dashboard user interface (e.g., within the dashboard GUI 200). This enables the top revenue opportunities section to display the top five opportunities with the revenue on the right-hand site of a bubble chart.

In an example, the set of APIs includes an API that returns the data for an operational process view dashboard user interface (e.g., within the dashboard GUI 200) which can be grouped by facility or modality. For instance, this API may return exam access wait, patient wait, scanning, image review time and diagnostics turnaround time.

In an example, the set of APIs includes an API that returns procedure information (e.g., procedure type, exam count, revenue per exam and average procedure type for the procedure).

In an example, the set of APIs includes an API that returns patient information (e.g., patient types).

In an example, the set of APIs includes an API that returns facility information (e.g., facility summary information, detailed information).

In an example, the set of APIs includes an API that returns time-based volume information (e.g., based on selected facility, modality, date range combinations).

In an example, the set of APIs includes an API that returns the data for the referred exam information (e.g., a graph based on exam count charted versus date, with the total referral exams, referrals per month, and referral change in last 30 days).

In an example, the set of APIs includes an API that returns the radiologist utilization data with respect to exams duration and revenue, and also returns revenue per radiologist and exams per radiologist on daily basis.

In an example, the set of APIs includes an API that returns the utilization for each modality in percentage and revenue for each modality in dollars, and also returns procedure name with exam volume count and revenue per exam in dollars for each procedure.

In an example, the set of APIs includes an API that returns technologist utilization for a facility (e.g., Revenue per technologist, Technologist percentage utilization, Technologist name, Daily exams per technologist, Modality Types).

In an example, the set of APIs includes an API that returns procedure summary data (e.g., Procedure_id, Procedure_name, Exam_volume, Reimbursement_per_exam, Cost_per_exam, Total_revenue, Total_profit, Time_deviation).

In an example, the set of APIs includes an API that returns top procedures by exam volume (e.g., Procedure_id, Procedure_name, Exam_volume, Revenue).

In an example, the set of APIs includes an API that returns actual duration data (e.g., Actual Duration, Exam day, Exam month, Exam year, Scheduled Duration, Average actual duration, Procedure name, Deviation).

In an example, the set of APIs includes an API that returns procedure stages (e.g., Procedure name, Exam access wait, Patient wait, Scanning, Image review, Diagnostic turn around).

In an example, the set of APIs includes an API that returns a projection summary (e.g., current and projected statistics of Referrals, Exam Volume, Revenue, Cost).

In an example, the set of APIs includes an API that returns a procedure revenue cost projection (e.g., that includes revenue and cost and profit of each day as well as data to draw projected dotted lines in a chart).

In an example, the set of APIs includes an API that returns an exam volume projection (e.g., that includes exam volume of each week as well as data to draw projected dotted lines in a chart).

In an example, the set of APIs includes an API that returns an equipment utilization projection (e.g., that includes equipment utilization of each week as well as data to draw projected dotted lines in a chart).

In an example, the set of APIs includes an API that returns projection opportunity summary data (e.g., that includes the current and projected exam volume per day and projected revenue and cost).

In an example, the set of APIs includes an API that returns resource utilization projection data (e.g., that includes utilization of each week as well as data to draw projected dotted lines in a graph and also display data with opportunity, such as the value of upper sigma).

In an example, the set of APIs includes an API that returns facility maximum resource deviation from KPI (a Key Performance Indicator) (e.g., deviation related to impact percentile, scheduled duration, time deviation and actual duration, by facility).

In an example, the set of APIs includes an API that returns modality maximum deviation from KPI (e.g., deviation related to impact percentile, scheduled duration, time deviation and actual duration, by modality).

In an example, the set of APIs includes an API that returns maximum deviation from KPI (e.g., deviation related to impact percentile, scheduled duration, time deviation and actual duration, entity type data for resources, technologist and procedures for selected facility or modality).

In an example, the set of APIs includes an API that returns time-based (daily, weekly, monthly) deviation from KPI (e.g., deviation related to scheduled revenue per hour and actual revenue per hour based on daily, weekly or monthly filters).

In an example, the set of APIs includes an API that returns scanner maximum deviation from KPI (e.g., deviation related to impact value, utilization per week for that scanner, and count of exams and deviated exams per week by that scanner).

In an example, the set of APIs includes an API that returns procedure maximum deviation from KPI (e.g., deviation related to impact percentile, scheduled duration, time deviation and actual duration, entity type data for resources, technologist and procedures for selected facility or modality).

In an example, the set of APIs includes an API that returns technologist maximum deviation from KPI (e.g., deviation related to impact percentile, scheduled duration, time deviation and actual duration, entity type data for resources, facilities, modalities and procedures for selected technologist).

In an example, the set of APIs includes an API that returns a facility's maximum referral drop or decrease in KPI (e.g., ordering providers associated with all facilities with historical average, 30 days referral count and total revenue loss of providers).

In an example, the set of APIs includes an API that returns a modality's maximum referral drop or decrease in KPI (e.g., ordering providers associated with all modalities with historical average, 30 days referral count and total revenue loss of providers).

In an example, the set of APIs includes an API that returns a modality's referral drop opportunity in KPI (e.g., all modalities with respect to a facility dimension referral drop opportunity that indicates the impact value per modality for selected opportunity).

In an example, the set of APIs includes an API that returns a facility's referral drop opportunity in KPI (e.g., all facilities with respect to a modality dimension referral drop opportunity that indicates the impact value per modality for selected opportunity).

In an example, the set of APIs includes an API that returns a daily referral trend for referral drop opportunity in KPI (e.g., for all referrals with respect to a selected dimension bubble such as facility, modality and radiologist specialty, while also indicating referral count on an organization level).

In an example, the set of APIs includes an API that returns a maximum referral drop table in KPI (e.g., for all referrals with respect to selected dimension bubble such as facility, modality and radiologist specialty that indicates a historical average and last 30 days count and revenue loss for that referral);

In an example, the set of APIs includes an API that returns a turnaround time trend in KPI for a referral drop opportunity (e.g., data for turnaround time over the period of time for selected referral drop opportunity that indicates the trend line or organizational basis for all data).

In an example, the set of APIs includes an API that returns an access wait time trend KPI for a referral drop opportunity (e.g., data for exam access wait over the period of time for selected referral drop opportunity that indicates the trend line or organizational basis for all data).

In an example, the set of APIs includes an API that returns a facility's idle time KPI (e.g., data for modality with its idle time per day and revenue per hour).

In an example, the set of APIs includes an API that returns a facility's idle time table (e.g., data with all modalities with respect to selected facility from the KPI, in a table that indicates the total idle time, late patient start, late start patient not late, and on-schedule start).

In an example, the set of APIs includes an API that returns a modality's idle time KPI (e.g., data for facility with its idle time per day and revenue per hour).

In an example, the set of APIs includes an API that returns a modality's idle time table (e.g., data with all resources with respect to selected modality from the KPI, in a table that indicates the total idle time, late patient start, late start patient not late, and on scheduled start).

In an example, the set of APIs includes an API that returns an annual cost average by modality type across an organization (e.g., annual cost averages by modality type across organization, including a table with columns such as Modality Type, Expected Equipment life in years, Average Equipment cost for this modality type, Average annual maintenance charges, Average supplies cost per procedure, Average consumables cost per procedure, Average technologist wages).

In an example, the set of APIs includes an API that returns pre-calculated referral drop opportunities, and pre-calculated scheduled versus actual opportunities.

In an example, the set of APIs includes Respective APIs that provide and update facilities, scanner, and equipment details.

In an example, the set of APIs includes Respective APIs to obtain and update outliers.

Figure 3:
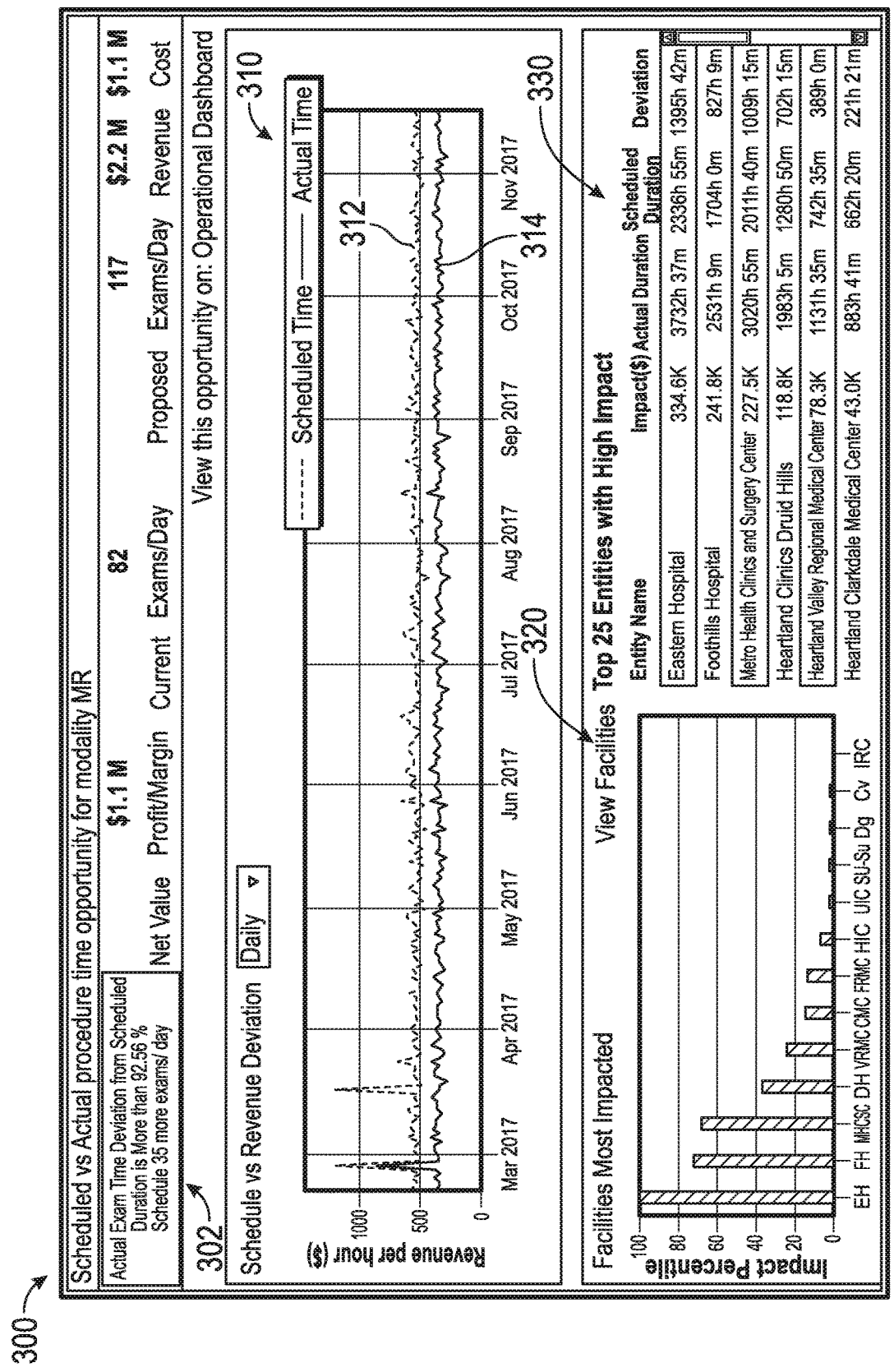
FIG. 3 illustrates a second graphical user interface of a data analytics system according to an example described herein.

In an example, the set of APIs includes an API that returns a GUI dashboard configuration, and configuration data, such as for configuration of a dashboard (e.g., the dashboard GUI 200 depicted in FIG. 2) or a detailed view (e.g., the detailed graphical user interface 300 depicted in FIG. 3). Aspects of these GUIs are discussed in the following paragraphs.

Graphical Display Functionality. FIG. 2 illustrates a first example of a graphical user interface 200 of a data analytics system, such as for use with the information system described herein. FIG. 3 illustrates a second example of a graphical user interface 300 of a data analytics system, such as for use with the information system described herein. In an example, the graphical user interface 200 includes various information outputs, dropdowns, menus, as part of a dashboard to visualize multiple types of opportunities for multiple analyzed entities (e.g., provider locations, health systems, or providers). The graphical user interface 300 includes a detailed view of a particular opportunity (Scheduled versus Actual Procedure Time Opportunity—for a particular modality type (MR)) which may be accessed by selecting an individual opportunity in the dashboard graphical user interface 200.

The dashboard graphical user interface 200 depicts a graphical charting 210 of opportunities. The charting 210 illustrates a plot of individual opportunities (respective circles) having a first axis indicating the amount or quantification of the opportunity (e.g., the "cost incurred" to perform the opportunity) relative to a value measurement or prediction of the opportunity (e.g., a "confidence score"). This charting 210 is further divided into sections, corresponding to the amount of the opportunity and the value measurement of the opportunity (e.g., risky opportunities, having low confidence scores; high cost opportunities, having high cost incurred but high confidence scores; best opportunities, having low cost incurred but high confidence scores). It will be understood that other data values may be plotted in the charting 210, such as amount of savings, amount of revenue, percentage increase, etc.

The dashboard graphical user interface 200 further illustrates a summarized view 220 of quantified values (e.g., revenue increases, cost savings) in connection with analyzing the opportunities. These may be aggregated by health system, facility, etc. among multiple opportunities or opportunity types, such as where the charting 210 illustrates individual values for medical facility sites but the summarized view 220 aggregates the individual values for an overall health system.

The dashboard graphical user interface 200 further illustrates summarized metrics 202 which can provide an overall status of analyzed operations and opportunities. For instance, the metrics 202 may illustrate an overall perspective of revenues, costs, equipment utilization, technologist utilization, radiologist relative value units (RVUs), number of exams, etc. These metrics 202 may be generated for historical data, forecasted data, or projected data tied to the selection of opportunities. It will be understood that other types of data and features may be provided within the dashboard graphical user interface 200 and like summary views.

The opportunity detailed view graphical user interface 300, in contrast, provides additional information on a specific type of opportunity. The detail graphical user interface 300 may include summarized metrics 302 for a status of an analyzed opportunity. For instance, the metrics 302 may include an indication of a projected or actual financial result (e.g., profit/margin, revenue, cost), and a comparison of opportunity activity (e.g., current number of exams, versus proposed number of exams). The metrics 302 may also provide a specific indication regarding the status of the opportunity (e.g., indicating the deviation of actual exam time duration from scheduled duration) along with a recommended action (e.g., schedule X more exams per day). In this fashion, the detail graphical user interface 300 provides an explanation of what the opportunity is, as well as how to respond to the opportunity.

The detail graphical user interface 300 also includes a graphical chart 310 of analytics relevant to the opportunity. For instance, a first value 312 (scheduled time) may be charted against a second value 314 (actual time), allowing the particular opportunity or analyzed value (here, deviation of procedure time) to be evident. Additionally, other types and forms of charts, listing, or comparisons may be present to provide data analytics. These include a comparison chart 320, illustrating the applicability of the opportunity to respective facilities or groups of facilities; and a comparison listing 330, illustrating the values relevant to applicability of the opportunity to respective facilities or groups of facilities.

In various examples, these or other forms of graphical user interfaces may provide graphical display functionality having the following characteristics and features (including in combination or separately). This list of characteristics and features is not exclusive.

In an example, the graphical user interface includes an organizational statistics ribbon that displays values indicating profit margins, utilization, revenue, cost, exam volume and referral volume (e.g., as part of a dashboard view). The graphical user interface may further include revenue and top-revenue opportunities depictions displayed as a bubble chart, with a filter menu that displays a Facilities, Modalities and Confidence score filter which are used to filter opportunities on an opportunities bubble chart, and a reset link to reset the filters to default values.

In an example, the graphical user interface includes a display of procedure statistics for a selected utilization revenue opportunity, such as provided by a bar chart and a table displayed for a selected utilization revenue opportunity, where a bar chart illustrates procedures versus exam volume, and the table illustrates procedures with a low revenue per exam and time taken to conduct that exam;

In an example, the graphical user interface includes a display of referral provider statistics for a selected utilization revenue opportunity, such as provided by a graph and a table displayed for a selected utilization revenue opportunity, where a graph shows daily referral count and a table indicates each of the referring providers with a drop in referrals;

In an example, the graphical user interface includes a display of average procedure time deviation for a modality for a selected opportunity, such as is provided by a graph and a table displayed for a selected utilization revenue opportunity, where a graph shows an average procedure time deviation and a table shows the time deviation at each stage in the procedure.

In an example, the graphical user interface includes a display of cost savings opportunities in a dashboard, such as provided by cost savings opportunities displayed as a bubble chart.

in an example, the graphical user interface includes a display of top cost savings opportunities in a dashboard, such as provided by top cost savings opportunities displayed as a bubble chart.

In an example, the graphical user interface includes a display of details for a selected utilization cost saving opportunity, such as Exam Volume and Scanner Utilization graphs that are shown on selection of any cost savings opportunities. For instance, an exam volume graph may show Exam count (for all scanners belonging to the same modality type in that facility) versus Period of analysis; a Scanner Utilization graph may show Scanner utilization (for all scanners belonging to the same modality type in that facility)—versus—Period of analysis.

In an example, the graphical user interface includes a display of Display Exam Count—versus—Procedure type, in a bar chart, for a selected cost saving opportunity. For instance, a bar graph and table may be shown on selection of any cost savings opportunities. For instance, a Bar graph may illustrate Exam count—versus—Exam Procedure type (for the selected scanner), and a Table illustrates the details for all the procedure codes that were performed on that scanner during the analysis period.

In an example, the graphical user interface includes a display of summary information of all procedures on an operational dashboard. This may include summary information to be displayed for all the procedures conducted during the analysis period, such as: Total revenue, Total cost incurred, and Equipment/Technologist/Radiologist utilization. In an example, the data displayed is illustrated with respect to the selected data filter set from a filter menu.

In an example, the graphical user interface includes a display of time duration blocks, such as displays of the time duration for each step in conducting a radiology procedure. For instance, the metrics displayed in procedure timeline may include: Exam access wait time, Patient wait time, Scanning time, Image review time and Diagnostic turnaround time.

In an example, the graphical user interface includes a display of Group data in the Operational dashboard process tab by Modality type or Facility. For instance, the data displayed in Operational dashboard process flow tab can be aggregated in terms of type of modality or by a particular facility. A user control such as a dropdown may also allow the user to switch between Modality and Facility grouping.

In an example, the graphical user interface includes a display of operational timelines based on process. For instance, an Operational process flow tab may display the time duration for each step in conducting a radiology procedure. The metrics displayed in procedure timeline may include Exam access wait time, Patient wait time, Scanning time, Image review time and Diagnostic turnaround time. The timeline chart may be updated when the user selects/deselects any procedure metrics option;

In an example, the graphical user interface includes a display of Facility-based summary details on a Facility Summary. For instance, a facility summary dashboard may provide the user with a detailed view at a facility level, indicating Facility Name, Modality utilization percentage, Exam Volume, Revenue in dollar units, and Percentage of Revenue share across all facilities in the integrated delivery network (IDN).

In an example, the graphical user interface includes a display of facility-based detailed information. The facility summary dashboard may provide the user with a detailed view at a facility level. For instance, this may include a ribbon to display summary information for that facility, along with Revenue per hour, Cost per hour, Revenue per exam, Modality utilization percentage, Technologist utilization percentage and Radiologist utilization percentage to be displayed.

In an example, the graphical user interface includes a display of Exam Volume details in a Facility detailed view. For instance, a bar graph and statistics may be shown on selection of any facility from a table; a bar graph shows the exam count in the selected facility for the period selected in the main filter; and statistics displayed on right side of the graph will show Total Exam count, Peak hours of the day and Peak day of the week for the selected period.

In an example, the graphical user interface includes a display of Modality utilization and Revenue details in a Facility detailed view. For instance, a three-axis bar graph and top procedures may be shown on selection of any facility from the table. A Bar graph shows different modality types versus percentage utilization of each modality. Top procedures table shows a full set of procedures done in the period, ordered by descending exam volume. A Modality Type dropdown is used to view the data for a specific modality in the top procedures table.

In an example, the graphical user interface includes a display of Technologist Utilization in Facility detailed view. For instance, a scatter plot and summary may be shown on selection of any facility from the table. The plot will show revenue in dollar units versus percentage utilization for a technologist, and a summary showing Revenue and Daily exams per technologist displayed on right side of the plot. The dropdown filter is used to view the scatter plot and summary details based on specific modality.

In an example, the graphical user interface includes a display of Radiologist utilization in Facility detailed view. For instance, a scatter plot and summary may be shown on selection of any facility from the table. The plot may show revenue in dollar units versus percentage utilization for a radiologist and summary showing Revenue and Daily exams per radiologist are displayed on right side of the plot. The dropdown filter may be used to view the scatter plot and summary details based on a specific modality or modality type.

In an example, the graphical user interface includes a display of Referring Provider View. For instance, a referring providers filter menu may display Date Range, Referred Facilities and Modalities filters which are used to filter Referring Providers.

In an example, the graphical user interface includes a display of summary information for a Referring Provider in a Referring Provider information view. For instance, a table is displayed for Referring providers. By default, the first Provider is selected. Also, the table is filtered based on inputs from Date or Facilities or Modalities filter.

In an example, the graphical user interface includes a display of a count of a number of Referred Exams on a daily basis in a Referring Providers view. For instance, a Referred Exams chart may be displayed for a selected Referring Provider. The chart data may be filtered based on inputs from a Date or Facilities or Modalities filter. An Up or Down arrow may be displayed indicating positive or negative slopes respectively for the selected Referring Provider. A table may be displayed to indicate the Total Referred Exams, Referrals per month and Referral drop in a time period (e.g., last 30 days).

In an example, the graphical user interface includes a display of Procedure-based summary information in a Procedures dashboard view. For instance, a table may be displayed for All Procedures. By default, the first Procedure is selected. Additionally, the table may be filtered based on inputs from Date or Facilities or Modalities filter.

In an example, the graphical user interface includes a display of Procedure details in the Procedure details dashboard view. For instance, Actual Duration and Procedure Stages chart may be displayed for a selected Procedure. The charts data may be filtered based on inputs from Date or Facilities or Modalities filter. An Actual Duration table may also indicate the Average Actual Duration, Scheduled Duration and Deviation in minutes and percentage. A table may also display the stages and their actual duration.

In an example, the graphical user interface includes a display of top procedures by Exam Volume chart in Referring Provider view. For instance, Top Procedures by Exam Volume chart may be displayed for a selected Referral provider. The chart data may be filtered based on inputs from Date or Facilities or Modalities filter. The chart may display the Exam Volume and Revenue for all the procedures.

In an example, the graphical user interface includes a display of Top ICD codes by Exam Volume in Referring Provider view. For instance, Top ICD codes by Exam Volume chart may be displayed for selected Referral provider. The chart data may be filtered based on inputs from Date or Facilities or Modalities filter. The chart may be used to display the Top ICD Codes by Exam Volume.

In an example, the graphical user interface includes a display of summary information, including Referrals, Exam Volume, Revenue and Costs for past or future date ranges.

In an example, the graphical user interface includes a display of Revenue and Procedure cost projection graph. For instance, a Revenue and Costs of Procedures chart may change on change of the filter menus, and be used to display the actual and projected Revenue and Costs.

In an example, the graphical user interface includes a Referrals and Exam Volume projection graph. For instance, an Exam Volume chart may be displayed on projection dashboard. The chart will change based on change of the filter menus, and used to display the actual and projected Exam Volume.

In an example, the graphical user interface includes an Equipment Capacity and Utilization graph. For instance, an Exam volume chart may be displayed on a usage dashboard. The chart may change based on change of the filter menus, and used to display the actual and projected Equipment Utilization.

In an example, the graphical user interface includes a display of a view scanner utilization opportunity. For instance, a Scanner Utilization chart may be displayed on opportunity-projection dashboard. The chart may be changed on change of the filter menus, and used to display the actual and projected Scanner Utilization with and without opportunities.

In an example, the graphical user interface includes a display of summary information of Scheduled versus Actual opportunity type in the ribbon. For instance, when a Scheduled versus Actual opportunity type bubble is selected, the summary information may be displayed below a dashboard. The Summary may change as per the filters applied on it. The Summary may contain net value of selected opportunity, current count of exams, proposed count of exams, additional revenue, and additional cost.

In an example, the graphical user interface includes a Profit projection graph. For instance, a Profit Margin chart may be displayed on projection dashboard. The chart will change on change of the filter menus. It will display the actual and projected Profit;

In an example, the graphical user interface includes a display of Facilities with maximum deviation impact KPI. For instance, when a bubble of scheduled opportunity type is selected, a bar chart for facilities with maximum impact may be shown, and display facilities in the form of bars arranged according to their impact percentile;

In an example, the graphical user interface includes a display of modalities with maximum deviation impact. For instance, when a bubble of scheduled opportunity type is selected, a bar chart for modalities with maximum impact may be shown, and display modalities in the form of bars arranged according to their impact percentile.

In an example, the graphical user interface includes a display of Facilities with details for maximum deviation impact KPI. For instance, when a bubble of scheduled opportunity type is selected, a bar chart for facilities with maximum impact may be shown.

In an example, the graphical user interface includes a display of Modalities with maximum deviation impact in a details table. For instance, when a bubble of scheduled opportunity type is selected, a bar chart for modalities with maximum impact is shown. As soon as the bar chart is loaded, corresponding table may be drawn.

In an example, the graphical user interface includes a display of Daily, Weekly and Monthly deviation impact KPI. For instance, when a bubble of scheduled opportunity type is selected a deviation graph for revenue may be displayed. This may include filters to filter data as per daily, monthly and weekly basis.

In an example, the graphical user interface includes a display of modalities (e.g., scanners) with maximum deviation impact. For instance, when a bubble of scheduled opportunity type is selected, a bar chart for scanners with maximum impact may be shown.

In an example, the graphical user interface includes a display of Technologists with maximum deviation impact. For instance, when a bubble of scheduled opportunity type is selected, a bar chart for technologists with maximum impact may be shown.

In an example, the graphical user interface includes a display of Procedures with maximum deviation impact. For instance, when a bubble of scheduled opportunity type is selected, bar chart for procedures with maximum impact may be shown.

In an example, the graphical user interface includes a display of Facilities with maximum referral drop impact for referral drop opportunity. For instance, when a referral drop bubble of type modality/specialty is selected, a bar chart for facilities with maximum referral drop may be shown.

In an example, the graphical user interface includes a display of Modalities with maximum referral drop impact for referral drop opportunity. For instance, when a referral drop bubble of type facility/specialty is selected, a bar chart for modalities with maximum referral drop may be shown.

In an example, the graphical user interface includes a display of daily referral trend based on dimension of the selected referral drop opportunity. For instance, when a bubble for referral drop opportunity is selected, a trend for daily referral drop may be shown.

In an example, the graphical user interface includes a display of access wait time trend for a referral drop opportunity. For instance, when a bubble for referral drop opportunity is selected, a trend for exam access wait time may be shown.

In an example, the graphical user interface includes a display Turnaround Time trend for a referral drop opportunity. For instance, when a bubble for referral drop opportunity is selected, a trend for diagnostic turnaround time may be shown;

In an example, the graphical user interface includes a display of Facilities with idle time relative to a KPI. For instance, when a bubble of Facility Resource Optimization opportunity type is selected, a scatter plot for facilities that have idle time may be shown.

In an example, the graphical user interface includes a display of Modalities with idle time relative to a KPI. For instance, when a bubble of Modality Resource Optimization opportunity type is selected, a scatter plot for modalities that have idle time may be shown.

In an example, the graphical user interface includes a display of annual cost averages by modality type across organization. For instance, this may include a view of the annual cost averages used for cost computation for each modality type.

In an example, the graphical user interface includes a display of Cost Computation in a Facilities detail view. For instance, a User may be able to view Facility Information such as Modality Costs and Equipment cost for that facility.

In addition to varying combinations of these graphical user interface features, various forms of summaries and interactive features may also be provided in a dashboard or other multi-function graphical user interface. Functional operations in the graphical user interface may include an Operational dashboard filter menu (e.g., that displays Date Range, Time Range, Facilities, Modalities, Patient Type and ICD Codes filters which are used to filter Operational dashboard, and a Reset Link is used to reset the filters to default values). Other filters for selecting time or data-based limits or conditions may also be implemented as extensions to the GUI features listed above.

In a specific example, the following approaches may be used for calculating confidence values of answers relevant to analyzed questions and opportunities. It will be understood that the confidence values referenced in the examples above may be calculated or generated by these or similar algorithms.

Confidence Scores. In an example, the information system may be utilized to identify a confidence score based on an aggregated metric calculated periodically, which is referred to in the following section as an averaged daily value or an average weekly value. This type of data is a time series. Unlike datasets with independent random samples, time series have an implicit order with the next value related to the previous value. For a confidence score, trending, seasonality, periodicity, etc., are not as important as the overall spread and variability of the data points: more stability means more confidence and less stability means less confidence.

The following methodology applies to any aggregated daily value or aggregated weekly value. In some examples, the following methodology will not work effectively for values aggregated at the monthly level because there won't be enough data; for example, an aggregated weekly dataset may only contain 26 points for a 6-month window, but at the monthly level, there may be only 6 data points, which may not be enough to determine a confidence value.

Within the time series input data, trending and periodicity is ignored. This does not necessarily involve applying detrending or de-seasonality calculations. Another approach called time lag analysis converts input time series data into independent samples allowing use of conventional statistical methods.

For datasets containing daily values over a span of time, a lag time analysis is performed to check the assumption that the previous data point is somehow correlated to the next. For instance, to check daily rad center operational data, last Monday is compared to this Monday, a weekly period where lag=7 days. Each weekday is extracted from the input dataset into a temporary dataset W of m observations. Each adjacent pair of values is then compared and saved, producing a new dataset D of deltas with n−1 observations. From these deltas, statistical confidence calculations can be performed. This process is repeated for each day of the week within the dataset. For instance, a source medical facility may not be open seven days a week, so any closed days will not be counted in the calculations. All resulting daily confidence values are then averaged to get an ultimate confidence value. Weekly aggregated datasets, however, do not have a lag time component for analysis. Confidence can be calculated by passing the weekly data through the same mechanism as the daily confidence calculation. In this case, the daily confidence will be the final confidence value.

In an example, a method may be utilized to calculate a confidence value given an input data set X containing either a) weekly aggregated values or b) daily values from a single day-of-the-week. This method may include determining the number of bins, creating an array D of proportional differences between adjacent values of X, Creating a weighting vector, one value for each bin, and calculating weighted range across all bins, and calculating confidence based on date ranges.

In further examples, the techniques above for confidence calculation may be further customized, according to aspects of binning, weighting, and outlier removal. In an example, binning may include values that are more recent in time, as such values are thought to be more important to the overall confidence compared to values farther away in time. To apply a weighting value, input data must be divided into regions, or bins, and then analyzed. Outliers within each region are identified and removed from consideration when calculating regional values. Intermediate confidence values for each region may be weighted and then summed to produce a final confidence value.

In an example, the binning process can be optimized by adjusting total number of bins needed, or adjusting bin size.

More bins allow more effect from weighting the data. But a minimum number of items are needed in each individual bin to make the confidence calculation useful. A reasonable compromise between the two ideas is to introduce overlapping bins. In an example, a half-lap of bins is used. Any leftover points most recent in time are included with the last full bin. In concept, overlap could be set to one third, one quarter, etc. where the lap value remains the same throughout the confidence calculation.

In an example, a linear descent produces the desired effect of reducing importance of older values using weighting. A sigmoid function (returns a better performing weighting by placing more emphasis on the right-hand side while de-emphasizing the left-hand side. After binning, calculating mean and standard deviation may be performed to identify "outliers" or perhaps more precisely, "undesirable" points within the given deltas. Such points include office days that are holidays with low traffic, or high volume days.

Confidence Score Scenario for Scheduled vs Actual Exam Duration. In an example, the following recommendation provides guidance to identify a confidence score for a scheduled versus an actual exam duration opportunity use case. This recommendation may be provided independent of site, modality, resource, technologist, etc. There is difficulty in producing this confidence, because radiological examination times vary by procedure and are scheduled in sessions as short 5 minutes (a typical x-ray of a hand), to up to 180 minutes and longer, or even longer for radiology procedures performed in conjunction with a surgery. Therefore, aggregate exam durations values should not be used across procedures. Further, patient encounter exam times have natural sources of noise (unexplained differences given the data) and variation (explainable differences such as this resource is older and takes more time to capture an image).

Additionally, each procedure has its own distribution of actual exam data, its own outliers, and a scheduled time. Exam data statistics represent the reality of durations for a given procedure. Confidence thus is an attribute derived by comparing a procedure's actual median duration to the scheduled duration. When median and schedule align, there is high confidence because reality matches expectations. As a schedule drifts from its median toward the extremities of the distribution, confidence diminishes. When the schedule is beyond the extremities, there is no real confidence because the schedule is not connected to reality.

Figure 4:
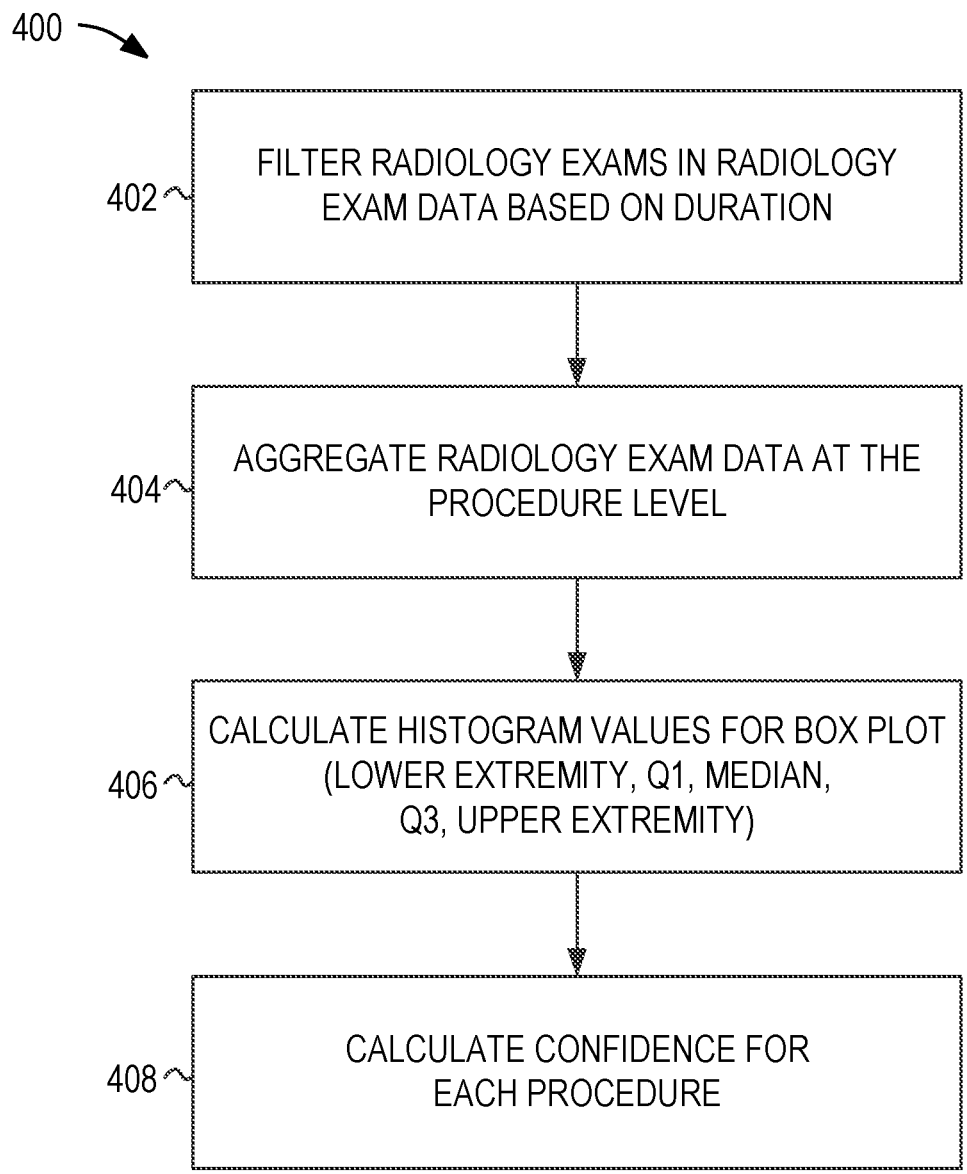
FIG. 4 illustrates a flowchart of a process for generating a confidence of a data value determined from medical imaging procedure data according to an example described herein.

FIG. 4 illustrates a flowchart 400 of a method applied for generating a confidence of a data value determined from medical imaging procedure data. This method may also be used to identify a confidence score at the procedure level. Accordingly, analyzing confidence values is an activity independent from identifying specific exams and their durations for considerations in an opportunity. Continuing the introduced example, scheduled versus actual exam duration confidence may be defined as follows:

Operation 402: Filter radiology exams in the set of radiology exam data based on duration. For instance, filter out any exam with a duration of <=3 minutes or more than 180 minutes (3 hours); and filter out any exam without an associated scheduled procedure duration value.

Operation 404: Aggregate radiology examination data at the procedure level, filtering out any procedures with fewer than 10 exams.

Operation 406: Calculate histogram values. For instance, this may include calculating the following values for each group using a Tukey box plot method: lower extremity, Q1, Median, Q3, upper extremity.

Operation 408: Calculate confidence for each procedure. When using exam durations to present an opportunity, apply confidence to each exam in the result. When selecting across time, such as the last three months, there may not be enough data to suggest anything meaningful as the procedure count goes to zero.

In an example, the confidence score produced is a linear function scheduled duration expressed as distance from extremity to median. Alternatively, a non-linear function could emphasize procedures where schedule is closer to median and deemphasize more quickly schedules farther away from their median. This method works when a procedure's scheduled duration is consistent across sites, which may not be the true. If this scheduled duration is consistent, procedure confidence should be aggregated at the site level. In an example, the generated probability and differences between data such as scheduled versus actual time may be depicted in analytics and graphical views.

It will be understood that other types of algorithms or functions may be used to calculate and represent confidence values as part of the presently described data analytics functions. Further, some analyzed or suggested opportunities may not involve any type of confidence calculation or confidence score display, as such analyzed or suggested opportunities may be directly compared and offered as an operational improvement, within a graphical user interface.

Figure 5:
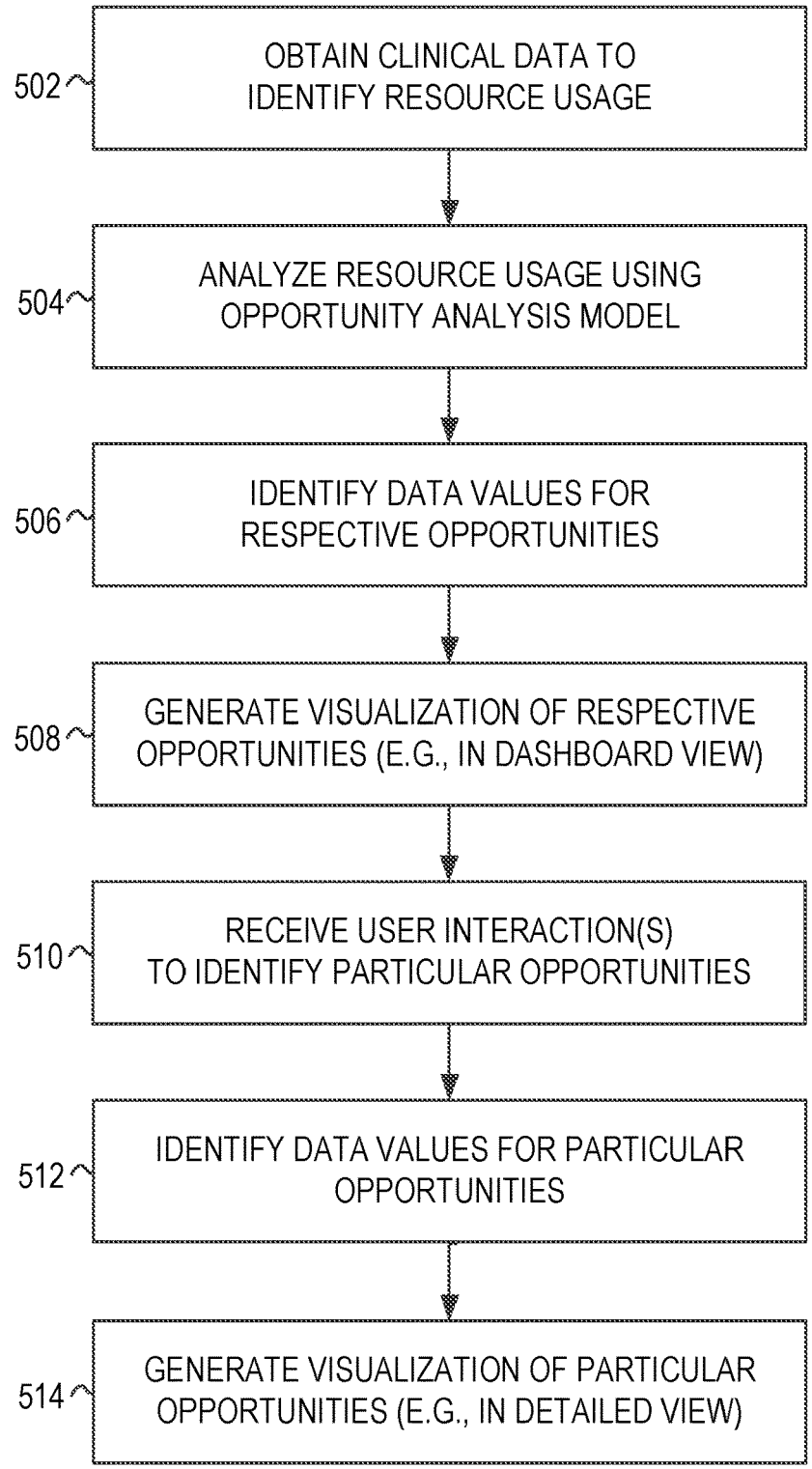
FIG. 5 illustrates a flowchart of process of performing opportunity and usage analytics on medical imaging procedure data according to an example described herein.

FIG. 5 illustrates a flowchart 500 of an example method of performing opportunity and usage analytics on medical imaging procedure data, further to the examples provided above. It will be understood that the following method operations are described from the perspective of an information processing system (e.g., server) which generates data and visualizations for output (e.g., in a client computing system, via a website, app, etc.). However, the following method operations may be equally implemented from another perspective (e.g., at the client, via client processing software) or with the involvement of multiple entities.

The flowchart 500 begins at operation 502 to obtain clinical data to identify resource usage. In an example, this operation includes obtaining a set of clinical data from an electronic data source, with the set of clinical data relating to a medical imaging procedure type. Such clinical data may indicate usage of respective imaging resources to perform a plurality of medical imaging procedures of the medical imaging procedure type (e.g., a computed tomography (CT), computed radiography (CR), digital radiography (DR), magnetic resonance (MR), Mammography (MG), X-ray, or ultrasound (US) imaging procedure). In further examples, the electronic data source includes information obtained for the plurality of medical imaging procedures from at least one of: a Health Level Seven (HL7) data source, a Digital Imaging and Communications in Medicine (DICOM) data source, a medical billing data source, a Centers for Medicare and Medicaid Services (CMS) reference data source, or an International Statistical Classification of Diseases revision 10 (ICD-10) data source.

The flowchart 500 continues at operation 504 to analyze resource usage, using one or more algorithms in an opportunity analysis model (or, combination of models or algorithms). In an example, analyzing the usage of the respective imaging resources from the clinical data, with the model, identifies values of respective opportunities for predicted changes to the usage of the respective imaging resources. In further examples, the respective imaging resources are associated with at least one of: a particular imaging modality, a particular medical facility, a particular health system, or a particular professional staffing. In some examples, the respective opportunities relate to a plurality of types of medical imaging procedures respectively performed by a plurality of medical providers at a plurality of locations.

Also in further examples, the opportunity analysis model is adapted to identify the values of the respective opportunities from at least one opportunity type, with the at least one opportunity type defined as at least one of: a resource utilization opportunity providing a measurement for revenue or cost savings for the usage among the respective imaging resources; a schedule utilization opportunity providing a measurement of additional procedures for increasing the usage among the respective imaging resources; a scheduled versus actual time utilization opportunity providing a measurement of deviation between scheduled usage and the usage among the respective imaging resources; a referral change opportunity providing a measurement in a change for the usage among the respective imaging resources as associated with respective referral sources; or an idle time optimization opportunity providing a measurement of an inactive state for the usage among the respective imaging resources.

Based on the analysis of resource usage, various data values are identified for respective opportunities, at operation 506. In an example, this may accompany analyzing the usage of the respective imaging resources and the predicted changes to the usage of the respective imaging resources, to identify monetary values associated with the values of the respective opportunities. Further, these data values may be identified from the opportunity analysis model which produces values for the respective opportunities, based on changes in at least one of: relative value units (RVUs), cost incurred, utilization rate, scheduling deviation, number of imaging procedures, revenue from imaging procedures, or cost of imaging procedures.

The flowchart 500 continues at operation 508 to generate a visualization of respective opportunities, such as in a dashboard view (e.g., in dashboard graphical user interface 200). In an example, the visualization of values for the respective opportunities is produced for output in a graphical user interface, with the visualization indicating positions of the values of respective opportunities relative to the usage of the respective imaging resources and the predicted changes to the usage of the respective imaging resources. In a further example, the visualization is provided by a graphical chart indicating values among the opportunities for a plurality of locations, the values charted on a first axis indicating confidence values for the predicted changes to the usage of the respective imaging resource, and a second axis indicating an opportunity value amounts for the predicted changes to the usage of the respective imaging resource.

The flowchart 500 continues at operation 510 to receive one or more user interactions, to identify or drill down on particular opportunities. In an example, the values charted in the dashboard graphical chart are selectable to obtain an opportunity view detail visualization, as the opportunity view detail visualization provides details for the predicted changes to the usage of the respective imaging resource, relative to at least one: health care system, medical facility, medical provider, imaging modality type, imaging modality device, staffing arrangement, or imaging procedure protocol. Thus, similar operations are performed at operation 512 to identify values for one or more particular opportunities, and at operation 514 to generate this visualization of the particular opportunities such as in a detailed visualization (e.g., in detailed view graphical user interface 300). In an example, the detail visualization portrays an application of the predicted changes among the respective imaging resources and facilities hosting the respective imaging resources.

Other variations to the operations 502-514 may be implemented in accordance with the techniques discussed herein. In some examples, the visualization is provided to the graphical user interface through data communicated via at least one application programming interface. Additionally, in some examples, the visualization may include a consideration and display of confidence score information, such as produced by calculating confidence scores for the values of the respective opportunities, the confidence scores representing a likelihood in the predicted changes to the usage of the respective imaging resources, where the visualization of the values of the respective opportunities includes a representation of the respective scores.

Figure 6:
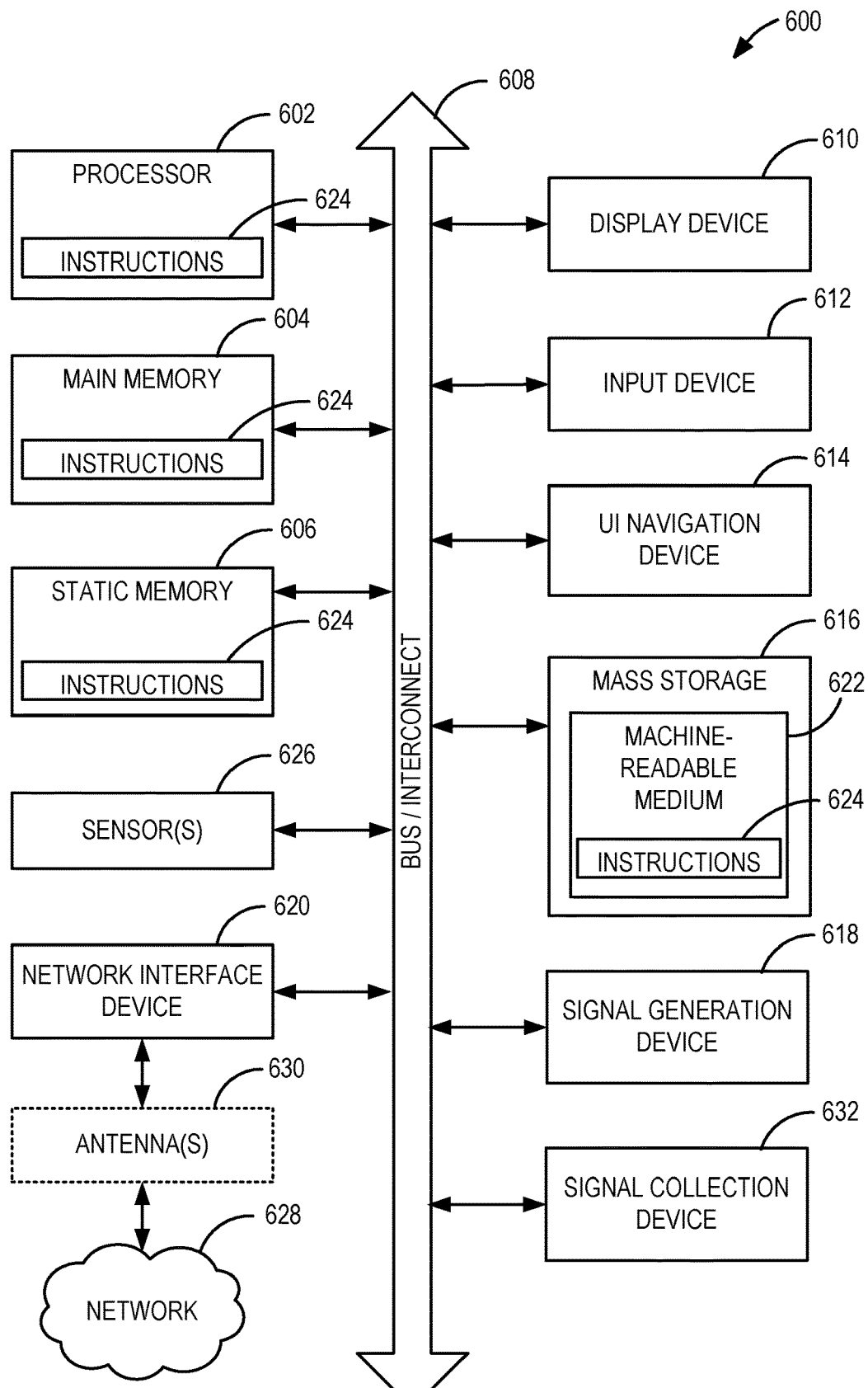
FIG. 6 illustrates an example of a machine configured to perform computing or electronic processing operations according to an example described herein.

FIG. 6 is a block diagram illustrating an example computing system machine upon which any one or more of the methodologies herein discussed may be run. Computer system 600 may be embodied as a computing device, providing operations of the components featured in the various figures, including any processing, storage, or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a Personal Digital Assistant (PDA), a mobile telephone or smartphone, a thin client, a web appliance, a virtual machine host, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 600 includes a processor 602 (e.g., a central processing unit (CPU), a graphics processing unit (GPU) or both), a main memory 604 and a static memory 606, which communicate with each other via an interconnect 608 (e.g., a link, a bus, etc.). The computer system 600 may further include a video display unit 610, an alphanumeric input device 612 (e.g., a keyboard), and a user interface (UI) navigation device 614 (e.g., a mouse). In one example, the video display unit 610, input device 612 and UI navigation device 614 are a touch screen display. The computer system 600 may additionally include a storage device 616 (e.g., a drive unit), a signal generation device 618 (e.g., a speaker), a signal collection device 632, and a network interface device 620 (which may include or operably communicate with one or more antennas 630, transceivers, or other wireless communications hardware), and one or more sensors 626.

The storage device 616 includes a machine-readable medium 622 on which is stored one or more sets of data structures and instructions 624 (e.g., software) embodying or utilized by any one or more of the methodologies or functions described herein. The instructions 624 may also reside, completely or at least partially, within the main memory 604, static memory 606, and/or within the processor 602 during execution thereof by the computer system 600, with the main memory 604, static memory 606, and the processor 602 also constituting machine-readable media.

While the machine-readable medium 622 is illustrated in an example to be a single medium, the term "machine-readable medium" may include a single medium or multiple media (e.g., a centralized or distributed database, and/or associated caches and servers) that store the one or more instructions 624. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 624 may further be transmitted or received over a communications network 628 using a transmission medium via the network interface device 620 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). Such communications may also be facilitated using any number of personal area networks, LANs, and WANs, using any combination of wired or wireless transmission mediums. The term "transmission medium" shall be taken to include any intangible medium that is capable of storing, encoding, or carrying instructions for execution by the machine, and includes digital or analog communications signals or other intangible medium to facilitate communication of such software.

The embodiments described above may be implemented in one or a combination of hardware, firmware, and software. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or a number of components, modules, or mechanisms. Such components may be tangible entities (e.g., hardware) capable of performing specified operations and may be configured or arranged in a certain manner. In an example, circuits may be arranged (e.g., internally or with respect to external entities such as other circuits) in a specified manner to implement such components. In an example, the whole or part of one or more computer systems (e.g., a standalone, client or server computer system) or one or more hardware processors may be configured by firmware or software (e.g., instructions, an application portion, or an application) that operates to perform specified operations. In an example, the software may reside on a machine readable medium. In an example, the software, when executed by the underlying hardware, causes the hardware to perform the specified operations.

Accordingly, such components may be a tangible entity that is physically constructed, specifically configured (e.g., hardwired), or temporarily (e.g., transitorily) configured (e.g., programmed) to operate in a specified manner or to perform part or all of any operation described herein. Considering examples in which such components are temporarily configured, each of the components need not be instantiated at any one moment in time. For example, where the components comprise a general-purpose hardware processor configured using software, the general-purpose hardware processor may be configured as respective different components at different times. Software may accordingly configure a hardware processor, for example, to constitute a particular component at one instance of time and to constitute a different component at a different instance of time.

Additional examples of the presently described method, system, and device embodiments are suggested according to the structures and techniques described above and specified in the following examples and claims.

For instance, Example 1 is a method for performing medical imaging resource usage analytics in a computing system, performed by electronic operations executed by processing circuitry of the computing system, with the electronic operations comprising: obtaining a set of clinical data from an electronic data source, the set of clinical data relating to a medical imaging procedure type, wherein the clinical data indicates usage of respective imaging resources to perform a plurality of medical imaging procedures of the medical imaging procedure type; analyzing the usage of the respective imaging resources from the clinical data, using an opportunity analysis model, the opportunity analysis model to identify values of respective opportunities for predicted changes to the usage of the respective imaging resources; and generating a visualization of the values of the respective opportunities for output in a graphical user interface, the visualization indicating positions of the values of respective opportunities relative to the usage of the respective imaging resources and the predicted changes to the usage of the respective imaging resources.

In Example 2, the subject matter of Example 1 includes, the electronic data source having information obtained for the plurality of medical imaging procedures from at least one of: a Health Level Seven (HL7) data source, a Digital Imaging and Communications in Medicine (DICOM) data source, a medical billing data source, a Centers for Medicare and Medicaid Services (CMS) reference data source, or an International Statistical Classification of Diseases revision 2 is missing parent: 2 is missing parent: 10 (ICD-10) data source; and wherein the medical imaging procedure type includes at least one of a: computed tomography (CT), magnetic resonance (MR), X-ray, or ultrasound (US) imaging procedure.

In Example 3, the subject matter of Examples 1-2 includes, the respective imaging resources being associated with at least one of: a particular imaging modality, a particular medical facility, a particular health system, or a particular professional staffing.

In Example 4, the subject matter of Examples 1-3 includes, the opportunity analysis model being adapted to identify the values of the respective opportunities from at least one opportunity type, wherein the at least one opportunity type includes at least one of: resource utilization opportunity, the resource utilization opportunity providing a measurement for revenue or cost savings for the usage among the respective imaging resources; schedule utilization opportunity, the schedule utilization opportunity providing a measurement of additional procedures for increasing the usage among the respective imaging resources; scheduled versus actual time utilization opportunity, the time utilization opportunity providing a measurement of deviation between scheduled usage and the usage among the respective imaging resources; referral change opportunity, the referral change opportunity providing a measurement in a change for the usage among the respective imaging resources as associated with respective referral sources; or idle time optimization opportunity, the idle time optimization opportunity providing a measurement of an inactive state for the usage among the respective imaging resources.

In Example 5, the subject matter of Examples 1-4 includes: analyzing the usage of the respective imaging resources and the predicted changes to the usage of the respective imaging resources, to identify monetary values associated with the values of the respective opportunities; generating a representation of the monetary values associated with the values of the respective opportunities for output in the graphical user interface.

In Example 6, the subject matter of Examples 1-5 includes, the opportunity analysis model operating to identify the values of the respective opportunities, based on changes in at least one of: radiologist value units, cost incurred, utilization rate, scheduling deviation, number of imaging procedures, revenue from imaging procedures, or cost of imaging procedures.

In Example 7, the subject matter of Examples 1-6 includes, the visualization being provided by a graphical chart indicating values among the opportunities for a plurality of locations, the values charted on a first axis indicating confidence values for the predicted changes to the usage of the respective imaging resource, and a second axis indicating an opportunity value amounts for the predicted changes to the usage of the respective imaging resource.

In Example 8, the subject matter of Example 7 includes, the values charted in the graphical chart being selectable to obtain an opportunity view detail visualization, wherein the opportunity view detail visualization provides details for the predicted changes to the usage of the respective imaging resource, relative to at least one: health care system, medical facility, medical provider, imaging modality type, imaging modality device, staffing arrangement, or imaging procedure protocol.

In Example 9, the subject matter of Examples 1-8 includes, the visualization being provided to the graphical user interface through data communicated via at least one application programming interface.

In Example 10, the subject matter of Examples 1-9 includes, the respective opportunities relating to a plurality of types of medical imaging procedures respectively performed by a plurality of medical providers at a plurality of locations.

In Example 11, the subject matter of Example 10 includes: calculating confidence scores for the values of the respective opportunities, the confidence scores representing a likelihood in the predicted changes to the usage of the respective imaging resources, wherein the visualization of the values of the respective opportunities includes a representation of the respective scores.

In Example 12, the subject matter of Examples 1-11 includes: receiving a user interaction with an illustration of a particular opportunity included in the visualization of the respective opportunities; and generating a detail visualization of the values of the particular opportunity for output in the graphical user interface, the detail visualization indicating an application of the predicted changes among the respective imaging resources and facilities hosting the respective imaging resources.

Example 13 is a machine-readable medium, including instructions, which when executed by a computing system, cause the computing system to perform any of the methods of Examples 1 to 12.

Example 14 is an apparatus comprising means for performing any of the methods of Examples 1 to 12.

Example 15 is a computing system, comprising a storage device to store a set of instructions, and processing circuitry including at least one processor to execute the set of instructions, wherein the set of instructions are provided from a plurality of components, and wherein the processing circuitry is arranged to execute instructions, with the at least one processor, to operate the plurality of components to perform any of the methods of Examples 1 to 12.

Example 16 is an information processing system, comprising: a storage device to store a set of instructions; and processing circuitry including at least one processor to execute the set of instructions, wherein the set of instructions are provided from a plurality of components including: a data request engine, the data request engine operable to request and receive a set of clinical data from an electronic data source, the set of clinical data relating to a medical imaging procedure type, wherein the clinical data indicates usage of respective imaging resources to perform a plurality of medical imaging procedures of the medical imaging procedure type; an algorithm data library, the algorithm data library including a plurality of executable algorithms, wherein the executable algorithms obtained from the algorithm data library include, an algorithm operable to analyze the usage of the respective imaging resources from the clinical data, via execution of the executable algorithms, to identify values of respective opportunities for predicted changes to the usage of the respective imaging resources; a visualization results engine, the visualization results engine operable to generate a visualization of the values of the respective opportunities for output in a graphical user interface, the visualization indicating positions of the values of respective opportunities relative to the usage of the respective imaging resources and the predicted changes to the usage of the respective imaging resources.

In Example 17, the subject matter of Example 16 includes, the electronic data source having information obtained for the plurality of medical imaging procedures from at least one of: a Health Level Seven (HL7) data source, a Digital Imaging and Communications in Medicine (DICOM) data source, a medical billing data source, a Centers for Medicare and Medicaid Services (CMS) reference data source, or an International Statistical Classification of Diseases revision 10 (ICD-10) data source; wherein the medical imaging procedure type includes at least one of a: computed tomography (CT), magnetic resonance (MR), X-ray, or ultrasound (US) imaging procedure; and wherein the respective imaging resources are associated with at least one of: a particular imaging modality, a particular medical facility, a particular health system, or a particular professional staffing.

In Example 18, the subject matter of Examples 16-17 includes, wherein the respective opportunities relate to a plurality of types of medical imaging procedures respectively performed by a plurality of medical providers at a plurality of locations; wherein the visualization is provided by a graphical chart indicating values among the opportunities for the plurality of locations, the values charted on a first axis indicating confidence values for the predicted changes to the usage of the respective imaging resource, and a second axis indicating an opportunity value amounts for the predicted changes to the usage of the respective imaging resource; and wherein the values charted in the graphical chart are selectable to obtain an opportunity view detail visualization, wherein the opportunity view detail visualization provides details for the predicted changes to the usage of the respective imaging resource, relative to at least one: health care system, medical facility, medical provider, imaging modality type, imaging modality device, staffing arrangement, or imaging procedure protocol.

In Example 19, the subject matter of Examples 16-18 includes, the executable algorithms obtained from the algorithm data library including an algorithm operable to calculate confidence scores for the values of the respective opportunities, the confidence scores representing a likelihood in the predicted changes to the usage of the respective imaging resources, wherein the visualization of the values of the respective opportunities includes a representation of the respective scores.

In Example 20, the subject matter of Examples 16-19 includes, the visualization results engine further operable to generate a detail visualization of the values of a particular opportunity for output in the graphical user interface, the detail visualization indicating an application of the predicted changes among the respective imaging resources and facilities hosting the respective imaging resources.

In Example 21, the subject matter of Examples 16-20 includes, further integration of any of the methods of Examples 1 to 12 into the information processing system or related server, client, or data processing computing systems.

What is claimed is:

1. A method for generating a graphical user interface of medical imaging resource usage analytics in a computing system, performed by electronic operations executed by processing circuitry of the computing system, with the electronic operations comprising:
    obtaining a set of clinical data from an electronic data source, the set of clinical data relating to a medical imaging procedure type, wherein the clinical data indicates usage of respective imaging resources to perform a plurality of medical imaging procedures of the medical imaging procedure type;
    analyzing the usage of the respective imaging resources from the clinical data, using an opportunity analysis model, the opportunity analysis model comprising at least one algorithm that is trained to generate resource usage values that optimize the usage of the respective imaging resources for at least idle time and schedules of the respective imaging resources;
    generating a visualization of the resource usage values for output in a graphical user interface, the visualization indicating positions of the resource usage values generated for each of the respective imaging resources and the optimized usage of the respective imaging resources;
    analyzing the usage of the respective imaging resources and the optimized usage of the respective imaging resources, using the opportunity analysis model, the at least one algorithm of the opportunity analysis model further trained to generate monetary values associated with the resource usage values generated for each of the respective imaging resources; and
    generating a representation of the monetary values associated with the resource usage values for output in the graphical user interface, the representation of the monetary values being a circle having a magnitude according to a respective monetary value displayed as a bubble chart.

2. The method of claim 1,
    wherein the electronic data source includes information obtained for the plurality of medical imaging procedures from at least one of: a Health Level Seven (HL7) data source, a Digital Imaging and Communications in Medicine (DICOM) data source, a medical billing data source, a Centers for Medicare and Medicaid Services (CMS) reference data source, or an International Statistical Classification of Diseases revision 10 (ICD-10) data source; and
    wherein the medical imaging procedure type includes at least one of a: computed tomography (CT), computed radiography (CR), digital radiography (DR), magnetic resonance (MR), Mammography (MG), X-ray, or ultrasound (US) imaging procedure.

3. The method of claim 1, wherein the respective imaging resources are associated with at least one of: a particular imaging modality, a particular medical facility, a particular health system, or a particular professional staffing.

4. The method of claim 1, wherein the opportunity analysis model is adapted to generate the resource usage values from at least one opportunity type, wherein the at least one opportunity type includes at least one of:
    resource utilization opportunity, the resource utilization opportunity providing a measurement for revenue or cost savings for the usage among the respective imaging resources;
    scheduled versus actual time utilization opportunity, the time utilization opportunity providing a measurement of deviation between scheduled usage and the usage among the respective imaging resources;
    referral change opportunity, the referral change opportunity providing a measurement in a change for the usage among the respective imaging resources as associated with respective referral sources, or
    idle time optimization opportunity, the idle time optimization opportunity providing a measurement of an inactive state for the usage among the respective imaging resources.

5. The method of claim 1, wherein the opportunity analysis model operates to generate the resource usage values, based on changes in at least one of: radiologist value units, cost incurred, utilization rate, scheduling deviation, number of imaging procedures, revenue from imaging procedures, or cost of imaging procedures.

6. The method of claim 1, wherein the visualization of the resource usage values is provided by a graphical chart indicating values for a plurality of locations, the values charted on a first axis indicating confidence values for the optimized usage of the respective imaging resource, and a second axis indicating an opportunity value amounts for the optimized usage of the respective imaging resource, and wherein the confidence values indicate a higher value as a distance between a median in histogram of usage of the imaging resources and the optimized usage decreases.

7. The method of claim 6, wherein the values charted in the graphical chart are selectable to obtain an opportunity view detail visualization, wherein the opportunity view detail visualization provides details for the optimized usage of the respective imaging resource, relative to at least one: health care system, medical facility, medical provider, imaging modality type, imaging modality device, staffing arrangement, or imaging procedure protocol.

8. The method of claim 1, wherein the visualization is provided to the graphical user interface through data communicated via at least one application programming interface.

9. The method of claim 1, wherein the resource usage values relate to a plurality of types of medical imaging procedures respectively performed by a plurality of medical providers at a plurality of locations.

10. The method of claim 9, the electronic operations further comprising:
calculating confidence scores for the values of the resource usage values, the confidence scores representing a distance between a median in histogram of usage of the imaging resources and the optimized usage, wherein the visualization of the values of the resource usage values includes a representation of the respective confidence scores.

11. The method of claim 1, the electronic operations further comprising:
receiving a user interaction with an illustration of a particular opportunity included in the visualization of the resource usage values; and
generating a detail visualization of the values of the particular opportunity for output in the graphical user interface, the detail visualization indicating an application of the optimized usage among the respective imaging resources and facilities hosting the respective imaging resources.

12. An information processing system, comprising:
a storage device to store a set of instructions; and
processing circuitry including at least one processor to execute the set of instructions, wherein the set of instructions are provided from a plurality of components including:
a data request engine, the data request engine operable to request and receive a set of clinical data from an electronic data source, the set of clinical data relating to a medical imaging procedure type, wherein the clinical data indicates usage of respective imaging resources to perform a plurality of medical imaging procedures of the medical imaging procedure type;
an algorithm data library, the algorithm data library including a plurality of executable algorithms, wherein the executable algorithms stored in the algorithm data library include at least one trained algorithm, that when executed, is operable to (i) analyze the usage of the respective imaging resources from the clinical data to generate resource usage values that optimize the usage of the respective imaging resources for at least idle time and schedules of the respective imaging resources and (ii) analyze the usage of the respective imaging resources and the optimized usage of the respective imaging resources to generate monetary values associated with the resource usage values generated for each of the respective imaging resources, wherein the at least one algorithm is to be implemented in a trained model; and
a visualization results engine, the visualization results engine operable to generate (i) a visualization of the resource usage values for output in a graphical user interface, the visualization indicating positions of the resource usage values generated for each of the respective imaging resources and the optimized usage of the respective imaging resources, and (ii) a representation of the monetary values associated with the resource usage values for output in the graphical user interface, the representation of the monetary values being a circle having a magnitude according to a respective monetary value displayed as a bubble chart.

13. The system of claim 12,
wherein the electronic data source includes information obtained for the plurality of medical imaging procedures from at least one of: a Health Level Seven (HL7) data source, a Digital Imaging and Communications in Medicine (DICOM) data source, a medical billing data source, a Centers for Medicare and Medicaid Services (CMS) reference data source, or an International Statistical Classification of Diseases revision 10 (ICD-10) data source;
wherein the medical imaging procedure type includes at least one of a: computed tomography (CT), computed radiography (CR), digital radiography (DR), magnetic resonance (MR), Mammography (MG), X-ray, or ultrasound (US) imaging procedure; and
wherein the respective imaging resources are associated with at least one of: a particular imaging modality, a particular medical facility, a particular health system, or a particular professional staffing.

14. The system of claim 12,
wherein the resource usage values relate to a plurality of types of medical imaging procedures respectively performed by a plurality of medical providers at a plurality of locations;
wherein the visualization is provided by a graphical chart indicating values for the plurality of locations, the values charted on a first axis indicating confidence values for the optimized usage of the respective imaging resource, and a second axis indicating an opportunity value amounts for the optimized usage of the respective imaging resource, and wherein the confidence values indicate a higher value as a distance between a median in histogram of usage of the imaging resources and the optimized usage decreases; and
wherein the values charted in the graphical chart are selectable to obtain an opportunity view detail visualization, wherein the opportunity view detail visualization provides details for the optimized usage of the respective imaging resource, relative to at least one: health care system, medical facility, medical provider, imaging modality type, imaging modality device, staffing arrangement, or imaging procedure protocol.

15. The system of claim 12, wherein the executable algorithms obtained from the algorithm data library include an algorithm operable to calculate confidence scores for the values of the resource usage values, the confidence scores representing a distance between a median in histogram of usage of the imaging resources and the optimized usage, wherein the visualization of the values of the resource usage values includes a representation of the respective scores.

16. The system of claim 12, the visualization results engine further operable to generate a detail visualization of the values of a particular opportunity for output in the graphical user interface, the detail visualization indicating an application of the optimized usage among the respective imaging resources and facilities hosting the respective imaging resources.

17. A non-transitory machine-readable storage medium, comprising instructions stored thereon, wherein the instructions, which when executed by a computing system, cause the computing system to perform operations comprising:
obtaining a set of clinical data from an electronic data source, the set of clinical data relating to a medical imaging procedure type, wherein the clinical data indicates usage of respective imaging resources to perform a plurality of medical imaging procedures of the medical imaging procedure type;

analyzing the usage of the respective imaging resources from the clinical data, using an opportunity analysis model, the opportunity analysis model comprising at least one algorithm that is trained to generate resource usage values that optimize the usage of the respective imaging resources for at least idle time and schedules of the respective imaging resources;

generating a visualization of the resource usage values for output in a graphical user interface, the visualization indicating positions of the resource usage values generated for each of the respective imaging resources and the optimized usage of the respective imaging resources;

analyzing the usage of the respective imaging resources and the optimized usage of the respective imaging resources, using the opportunity analysis model, the at least one algorithm of the opportunity analysis model further trained to generate monetary values associated with the resource usage values generated for each of the respective imaging resources; and generating a representation of the monetary values associated with the resource usage values for output in the graphical user interface, the representation of the monetary values being a circle having a magnitude according to a respective monetary value displayed as a bubble chart.

18. The machine-readable storage medium of claim 17, wherein the electronic data source includes information obtained for the plurality of medical imaging procedures from at least one of:

a Health Level Seven (HL7) data source, a Digital Imaging and Communications in Medicine (DICOM) data source, a medical billing data source, a Centers for Medicare and Medicaid Services (CMS) reference data source, or an International Statistical Classification of Diseases revision 10 (ICD-10) data source, wherein the medical imaging procedure type includes at least one of a: computed tomography (CT), computed radiography (CR), digital radiography (DR), magnetic resonance (MR), Mammography (MG), X-ray, or ultrasound (US) imaging procedure; and wherein the respective imaging resources are associated with at least one of: a particular imaging modality, a particular medical facility, a particular health system, or a particular professional staffing.

19. The machine-readable storage medium of claim 17, wherein the opportunity analysis model is adapted to generate the resource usage values from at least one opportunity type, wherein the at least one opportunity type includes at least one of:

resource utilization opportunity, the resource utilization opportunity providing a measurement for revenue or cost savings for the usage among the respective imaging resources;

scheduled versus actual time utilization opportunity, the time utilization opportunity providing a measurement of deviation between scheduled usage and the usage among the respective imaging resources, referral change opportunity, the referral change opportunity providing a measurement in a change for the usage among the respective imaging resources as associated with respective referral sources; or idle time optimization opportunity, the idle time optimization opportunity providing a measurement of an inactive state for the usage among the respective imaging resources.

20. The machine-readable storage medium of claim 17, wherein the opportunity analysis model operates to generate the resource usage values, based on changes in at least one of: radiologist value units, cost incurred, utilization rate, scheduling deviation, number of imaging procedures, revenue from imaging procedures, or cost of imaging procedures.

21. The machine-readable storage medium of claim 17, wherein the visualization of the resource usage values is provided by a graphical chart indicating values for a plurality of locations, the values charted on a first axis indicating confidence values for the optimized usage of the respective imaging resource, and a second axis indicating an opportunity value amounts for the optimized usage of the respective imaging resource, and wherein the confidence values indicate a higher value as a distance between a median in histogram of usage of the imaging resources and the optimized usage decreases;

wherein the values charted in the graphical chart are selectable to obtain an opportunity view detail visualization, wherein the opportunity view detail visualization provides details for the optimized usage of the respective imaging resource, relative to at least one: health care system, medical facility, medical provider, imaging modality type, imaging modality device, staffing arrangement, or imaging procedure protocol.

22. The machine-readable storage medium of claim 17, wherein the visualization is provided to the graphical user interface through data communicated via at least one application programming interface.

* * * * *